US008610054B2

(12) United States Patent
Giles et al.

(10) Patent No.: US 8,610,054 B2
(45) Date of Patent: Dec. 17, 2013

(54) ION ANALYSIS APPARATUS AND METHOD OF USE

(75) Inventors: Roger Giles, West Yorkshire (GB); Dimitris Papanastasiou, Athens (GR)

(73) Assignee: Shimadzu Corporation, Kyoto-Shi (JP)

( * ) Notice: Subject to any disclaimer, the term of this patent is extended or adjusted under 35 U.S.C. 154(b) by 241 days.

(21) Appl. No.: 13/318,317

(22) PCT Filed: Apr. 30, 2010

(86) PCT No.: PCT/GB2010/000873
§ 371 (c)(1),
(2), (4) Date: Oct. 31, 2011

(87) PCT Pub. No.: WO2010/125357
PCT Pub. Date: Nov. 4, 2010

(65) Prior Publication Data
US 2012/0056085 A1    Mar. 8, 2012

(30) Foreign Application Priority Data
May 1, 2009 (GB) .................................. 0907619.1

(51) Int. Cl.
H01J 49/42 (2006.01)
H01J 49/04 (2006.01)
B01D 59/44 (2006.01)

(52) U.S. Cl.
USPC ............................ 250/282; 250/281; 250/288

(58) Field of Classification Search
USPC ........ 250/281–283, 288, 290–294; 96/15, 25, 96/51, 54, 67, 75
See application file for complete search history.

(56) References Cited

U.S. PATENT DOCUMENTS

| 6,900,433 B2 | 5/2005 | Ding |
| 7,060,987 B2* | 6/2006 | Lee et al. ................... 250/423 R |
| 7,091,481 B2* | 8/2006 | Miller et al. ................... 250/288 |

(Continued)

FOREIGN PATENT DOCUMENTS

| GB | 2382919 A | 6/2003 |
| GB | 2432255 A | 5/2007 |
| GB | 2443952 A | 5/2008 |
| GB | 2446960 A | 8/2008 |

(Continued)

OTHER PUBLICATIONS

Robert Guevremont et al., "Atmospheric pressure ion focusing in a high-field asymmetric waveform ion mobility spectrometer" Review of Scientific Instruments, vol. 70, No. 2, pp. 1370-1383, Feb. 1999.

(Continued)

Primary Examiner — Bernard E Souw
(74) Attorney, Agent, or Firm — Bingham McCutchen LLP

(57) ABSTRACT

The present invention is concerned with an ion analysis apparatus for conducting differential ion mobility analysis and mass analysis. In embodiments, the apparatus comprises a differential ion mobility device in a vacuum enclosure of a mass spectrometer, located prior to the mass analyzer, wherein the pumping system of the apparatus is configure to provide an operating pressure of 0.005 kPa to 40 kPa for the differential ion mobility device, and wherein the apparatus includes a digital asymmetric waveform generator that provides a waveform of frequency of 50 kHz to 25 MHz. Examples demonstrate excellent resolving power and ion transmission. The ion mobility device can be a multipole, for example a 12-pole and radial ion focusing can be achieved by applying a quadrupole field to the device in addition to a dipole field.

19 Claims, 13 Drawing Sheets

(56) References Cited

U.S. PATENT DOCUMENTS

| | | | |
|---|---|---|---|
| 7,528,365 B2* | 5/2009 | Guo et al. | 250/282 |
| 7,550,717 B1 | 6/2009 | Belford et al. | |
| 8,067,747 B2 | 11/2011 | Wollnik | |
| 2003/0020012 A1 | 1/2003 | Guevremont | |
| 2003/0089849 A1 | 5/2003 | Guevremont et al. | |
| 2004/0238755 A1* | 12/2004 | Lee et al. | 250/423 R |
| 2005/0121607 A1* | 6/2005 | Miller et al. | 250/287 |
| 2006/0255264 A1 | 11/2006 | Belford | |
| 2007/0262253 A1* | 11/2007 | Guo et al. | 250/283 |
| 2009/0173877 A1 | 7/2009 | Bateman et al. | |
| 2009/0283674 A1 | 11/2009 | Pesch | |
| 2010/0108879 A1 | 5/2010 | Bateman et al. | |

FOREIGN PATENT DOCUMENTS

| | | | |
|---|---|---|---|
| WO | 0063949 | A1 | 10/2000 |
| WO | 0250866 | A2 | 6/2002 |
| WO | 2007056488 | A1 | 5/2007 |
| WO | 2007136373 | A1 | 11/2007 |
| WO | 2008055667 | A2 | 5/2008 |
| WO | 2008067331 | A2 | 6/2008 |

OTHER PUBLICATIONS

Randy Purves et al., "Mass spectrometric characterization of a high-field asymmetric waveform ion mobility spectrometer" Review of Scientific Instruments, vol. 69, No. 12, pp. 4094-4105, Dec. 1998.

Erkinjon G. Nazarov et al., "Pressure Effects in Differential Mobility Spectrometry" Analytical Chemistry, vol. 78, No. 22, pp. 7697-7706, Nov. 15, 2006.

L. Ding et al., "Ion motion in the rectangular wave quadrupole field and digital operation mode of a quadrupole ion trap mass spectrometer" Rapid Communication in Mass Spectrometry, vol. 20, pp. 3-8, 2006.

Michael Guilhaus, "Essential elements of time-of-flight mass spectrometry in combination with the inductively coupled plasma ion source" Spectrochimica Acta Part B, vol. 55, pp. 1511-1525, Jun. 19, 2000.

I.A. Buryakov, et al., "A new method of separation of multi-atomic ions by mobility at atmospheric pressure using a high-frequency amplitude-asymmetric strong electric field" International Journal of Mass Spectrometry and Ion Processes, vol. 128, pp. 143-148, May 18, 1993.

D. Papanastasiou et al., "Differential Mobility Separation of Ions Using a Rectangular Asymmetric Waveform" J. Phys. Chem. A, vol. 112, pp. 3638-3645, Feb. 7, 2008.

Alexandre A. Shvartsburg et al., "Optimization of the Design and Operation of FAIMS Analyzers" J Am. Soc. Mass Spectrom., vol. 16, pp. 2-12, 2005.

UK search report dated Aug. 27, 2009 for corresponding UK application GB0907619.1 cites the foreign patent documents and U.S. patent application publications above.

* cited by examiner

Figure 12a
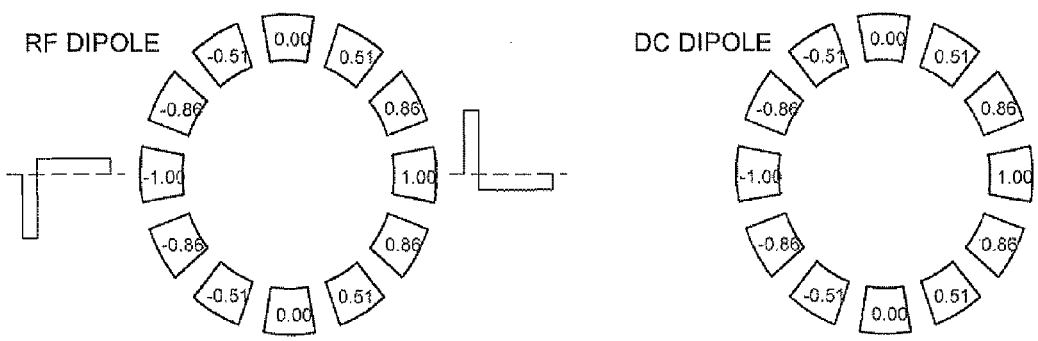
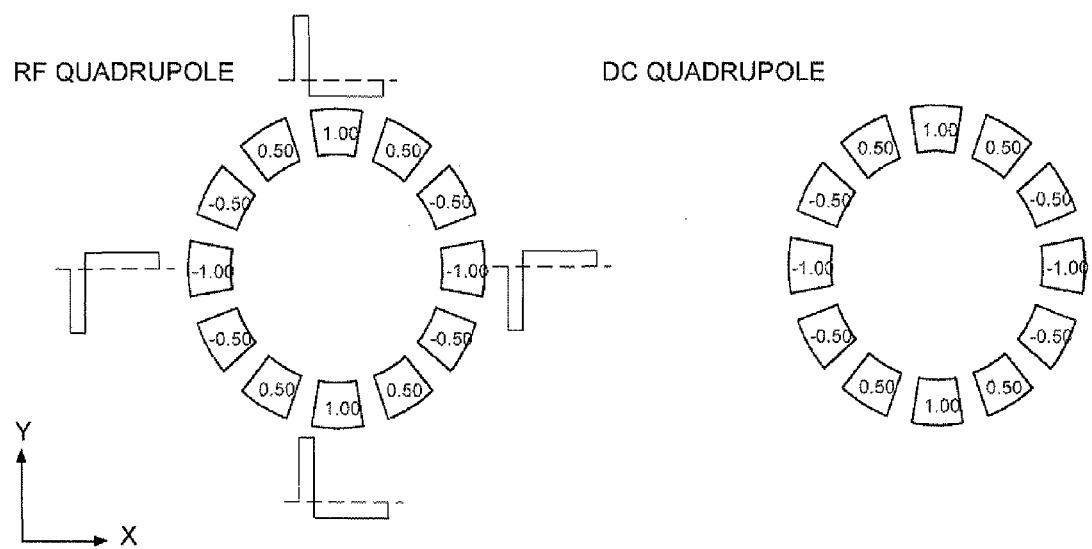
Figure 12b

Figure 13a
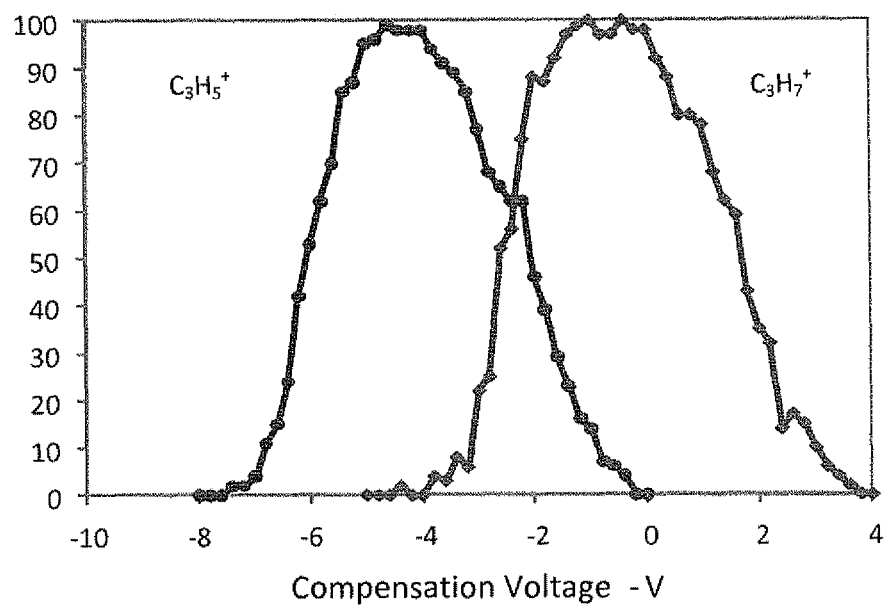
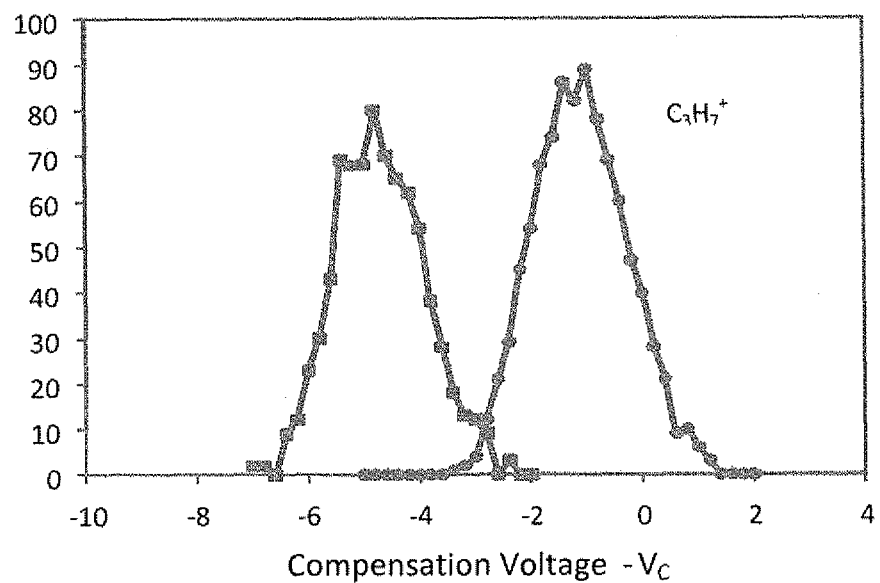
Figure 13b

ION ANALYSIS APPARATUS AND METHOD OF USE

CROSS-REFERENCE TO THE RELATED APPLICATIONS

This application is a national stage of international application No. PCT/GB2010/000873, filed on Apr. 30, 2010, and claims the benefit of priority under 35 USC 119 to United Kingdom Application No, 0907619.1, filed on May 1, 2009, the entire contents of which are incorporated herein by reference.

TECHNICAL FIELD OF THE INVENTION

The invention relates to differential ion mobility analysis and to mass spectrometers and in particular to the use of differential mobility spectrometry with mass spectrometry.

BACKGROUND OF THE INVENTION

Differential ion mobility spectrometry (DMS) is a technique based on the principles of ion mobility spectrometry (IMS). In IMS, ions are guided by an axial uniform electric field through a gas medium at constant pressure. The combined action of the driving force of the electric field accelerating the charged species and the damping force introduced by collisions between ions and the gas molecules results in an average drift velocity of the ions in the direction of the applied electric field.

Ion mobility is defined as the ratio of the average drift velocity of an ion group injected into the IMS cell over the applied electric field, $K=u_{Av}/E$. Therefore, the drift time of an ion through a given length is determined by the applied electric field and the mobility; the latter reflects the ion's collision cross section as well as the nature of the interactions between ions and the molecules comprising the gas medium. Ions having different collision cross sections, and depending on the nature of the interaction with the gas medium, will resolve into groups drifting with different average velocities through the cell. Separation in IMS relies primarily on variations in the volume/charge ratio of the ions.

Recent developments in IMS have been mainly driven by applications involving the structural elucidation of macromolecules in conjunction with the determination of their molecular masses using mass spectrometry (MS). Additional features that establish IMS as an indispensible tool in the analysis of complex samples is the separation of isobaric forms of compounds (that is, compounds having the same m/z ratio) and also the enhancement of the signal-to-noise ratio observed in a mass spectrum.

In so-called hyphenated IMS-MS instruments, the ion mobility drift cell is attached to the front-end of the mass spectrometer, externally to the mass spectrometer's vacuum enclosure, and operated at ambient pressure. Consequently, mobility separation is limited to ions generated in atmospheric pressure ionization sources. Atmospheric pressure IMS suffers from low efficiency of transmission of ions into the mass spectrometer's vacuum enclosure because diffusion causes expansion of the ion beam, which adversely affects sampling efficiency at the MS interface as ions must pass through a small aperture, typically 0.2 to 0.5 mm diameter.

Despite the fact that diffusion becomes more dominant at lower pressures and ion losses can become significant, ion optical devices can be inserted after the IMS device to re-gather ions. This has permitted the development of low pressure and vacuum IMS, which has considerably extended the range of IMS instruments and techniques available for the analysis of complex mixtures. Intermediate pressure IMS cells are compatible with virtually any vacuum ion source, in addition to available atmospheric pressure ionization sources. Separation of ions based on ion mobility has been performed at pressures as low as 0.1 mtorr. As with ambient pressure IMS, the ions exiting the IMS drift cell and ion optics can be delivered to the front-end of a mass spectrometer.

Ion mobility, K, varies non-linearly with variations on the applied electric field and pressure. This dependence is usually approximated by a series expansion of the mobility K in even powers of the parameter E/N where E is the electric field and N is the number gas density per Eq. (I) [E. A Mason, E. W. McDaniel, Transport Properties of Ions in Gases; Wiley, 1988]:

$$K(E/N)=K(0)[1+\alpha_2(E/N)^2+\alpha_4(E/N)^4+\ldots] \qquad (I)$$

The ion mobility at the zero field limit, K(0), is used to define the threshold below which the value of the average drift velocity scales linearly with electric field, that is, the ion mobility K(0) is constant and velocity is directly proportional to electric field, $u_{Av}=K(0)$ E. Drift cells operated at atmospheric pressure are usually operated below the zero field limit and the electric field gradient required to guide ions through the gas is greater as compared to drift cells operated at reduced pressures where the value of E/N may extend into the non-linear range of K. Ions are categorized using Eq. (I) and the corresponding mobility coefficients, or alpha coefficients, which determine the dependence of K on E/N. For A-type ions $\alpha_2>0$, $\alpha_4>0$ and mobility increases with E/N. The effect is reversed for C-type ions where the mobility decreases with E/N and $\alpha_2<0$, $\alpha_4<0$. A more complex behavior is obtained for B-type ions where $\alpha_2>0$, $\alpha_4<0$. The Townsend unit, Td, has been introduced to depict that the fundamental character of ion-molecule interactions in ion mobility is revealed by the dependence of K on the ratio of parameters E/N, where, 1 Td=$10^{-21}$ Vm$^2$.

Several techniques for separating ions based on the mobility properties of ionic species have been developed since the early work performed on drift cell IMS. In particular, differential mobility spectrometry (DMS) [I. A. Buryakov, et al, Int. J. Mass Spectrom. Ion Processes 1993, 128, 143], also known as field asymmetric ion mobility spectrometry (FAIMS) [R. W. Purves, et al, Rev. Sci. Instrum. 1998, 69, 4094], relies on the dependency of the ion mobility, K, on the applied electric field and number gas density, E/N. In contrast to IMS, the ions in DMS are entrained in a gas stream and oscillate in the presence of a periodic asymmetric waveform that alternates between a high-field and a reversed low-field. The electric field is applied perpendicularly to the direction of gas flow. Ions experience an average net displacement per waveform cycle depending on the differences between high- and low-mobility. This results in the ions drifting progressively off-axis and discharging on electrodes confining gas flow. The displacement can be compensated by a DC voltage and ions of a given mobility dependence can be transmitted successfully through the device. A spectrum is generated by scanning the compensation voltage at fixed amplitude and waveform frequency and collecting the transmitted ions either by using an electrometer or introducing them into the front end of a mass spectrometer.

Two principal DMS systems have been developed, depending on their ability to focus ions in the direction transverse to the gas flow. In the first type, ions are carried by gas flow confined between two concentric cylinders of different radii in a coaxial arrangement. The asymmetric waveform and the compensation voltage are usually applied to the inner electrode. The logarithmic field established between the two cylindrical electrodes has the ability to focus ions transversally and maintain high transmission at increased waveform amplitudes [R. Guevremont, R. W. Purves, Rev. Sci. Instrum. 1999, 70, 1370]. In the second configuration ions are forced to oscillate between two parallel plates, one of which carries the asymmetric periodic waveform and the compensation voltage while the opposite electrode is maintained at ground potential. The dipole field formed between the plates has no focusing properties and the number of ions lost on the electrodes is approximately proportional to the amplitude of the asymmetric waveform. Transmission through such a dipole field is possible for all types of ions, the types being categorized depending on the type of the non-linear dependence of K on E/N, in contrast to the cylindrical design where transportation becomes selective, that is, ions of a certain type can only be transmitted for a given waveform.

The present inventors have found that the performance and applications of DMS so far is limited due to a number of disadvantages associated with this relatively new technology. In particular, unlike IMS, the DMS devices described in the literature have been exclusively operated at ambient or subambient pressures and interfaced externally to the vacuum enclosure of a mass spectrometer.

Generally, the pumping rate provided by the inlet of the MS (e.g. a capillary or critical orifice) is in the region of $1 \text{ L min}^{-1}$, which has been found to be a convenient rate for pumping air slowly through the gap between the plates of a DMS or a FAIMS device. This provides the necessary laminar flow conditions for separation to occur.

Nevertheless, a disadvantage of operating at a fixed flow rate is that the predetermined residence time of the ions through the DMS cannot be easily adjusted for enhancing instrument performance. This is particularly true in the case where the separation gap between the DMS electrodes is also fixed. Operating the DMS at ambient or near ambient pressure and establishing high-field conditions (~100 Td) sufficient for inducing separation requires the minimum possible separation distance between the electrodes, which in turn limits the sampling efficiency of the system and compromises sensitivity. In particular, sampling by a MS of electrosprayed ions through the narrow gap of a DMS device becomes problematic. Furthermore, it is demonstrated experimentally that the transmitted ion current cannot exceed ~10 pA, which is significantly lower than the ion current generated in an electrospray ionization source [Shvartsburg at al, J. Am. Soc Mass Spectrom. 2005, 16, 2-12]. In summary, the number of ions available for analysis in the MS is much lower because of ion losses and restrictions on ion flow caused by the DMS.

To date, DMS devices are coupled to atmospheric pressure "soft" ionization sources, and in particular to the electrospray ionization source operated at relatively low flow rates $\sim 1 \text{ }\mu\text{L min}^{-1}$. This limitation is mainly imposed by the formation of bigger droplets when spraying at the higher flow rates, which, unless sufficient evaporation is allowed to occur, can significantly degrade the performance of the DMS. Since operation of such devices at ambient conditions are incapable of attaining the desired performance, accommodation of such high flow rates required for high throughput LC MS analysis using DMS as the front-end in MS platforms remains a goal.

Furthermore, the operation of a DMS device at ambient pressure is restricted to clean samples and liquid chromatography (LC) buffers not containing involatile salts. The direct analysis of "dirty" samples such as biological fluids can quickly compromise the DMS performance. Robust ionization sources have been developed to tolerate these types of samples, together with the involatile buffers used in aiding LC separations, however, they remain incompatible with the DMS interface to the MS.

Another limitation of the current DMS technology is the poor resolution, measured by the peak width in terms of the compensation voltage, which is limited to ~20 and appears to be significantly lower than that obtained in drift cell IMS. Methods to improve resolution are compromised by the narrow range of E/N at which DMS has been operated to date.

In a FAIMS device described in US 2003/0020012, parent ions generated from a sample undergo mass analysis in the normal way and then fragment ions produced by a collision cell are subjected to FAIMS separation. This requires the pressure in the FAIMS device to be compatible with the collision cell operating pressure. Specifically, parent ions are selectively transmitted through a first mass analyzer in a low pressure chamber, injected into a collision cell operating in a second pressure chamber operating at increased pressure (which second pressure chamber is located within the low pressure chamber) wherein fragmentation of the parent ions occurs in a collision cell.

Subsequently, the fragment ions are filtered by a FAIMS device prior to injection of the ions from the second pressure chamber back into the low pressure chamber for the second stage of mass analysis.

This geometry is intended only to separate fragment ions with equal ratios of m/z (isobaric ions) which would otherwise appear as a single spectral line when measured in the second mass analyzer. The pressure range established in the FAIMS device is therefore limited by the operational pressure of the collision cell. Indeed, the dedicated collision gas supply provided to the second pressure chamber dictates the pressure of the FAIMS device. Accordingly, a range of operating pressures is not available and hence the range of accessible E/N ratios is narrow.

In another DMS arrangement described by E. G. Nazarov at al, Anal in Chem, 2006, 78, 7697, ions are transported through a planar electrode system where pressure within the DMS may be adjusted by means of a system of flow controllers, needle valves and a miniature pump. The DMS is situated externally to a mass spectrometer and ions transported successfully through the gap between the planar electrodes are deflected by a DC bias into a 2 mm inlet hole and toward the inlet orifice of the mass spectrometer. Using this system the effect of pressure was investigated in the range of 0.4-1.55 atm (405-1570.5 mbar). A pressure of 0.6-0.8 atm was found to provide reduced dimerisation and high resolution. The present inventors have observed that transportation of the ions from the DMS to the mass spec relies to a great extent on gas flow and reducing the pressure differential across the MS interface has a significant effect on sensitivity. Thus, lowering the pressure below that studied by Nazarov et al would have an adverse affect on transport efficiency of the ions from the DMS through the inlet capillary or orifice of the MS.

Thus, at present, DMS and FAIMS devices are operated at and/or near ambient pressure and the value of E/N is limited to ~100 Td (1 Td=$10^{-21}$ Vm$^2$), which corresponds to ~1220 V across a 0.5 mm gap at ~1 atm=1013.25 mbar and 300 K. At these pressures breakdown events impose an upper limit to the amplitude of the waveform and therefore restrict the accessible range of the ratio E/N. Furthermore, ion transport from the DMS to the MS is inefficient.

SUMMARY OF THE INVENTION

At its most general, the present invention proposes that a DMS device (e.g. one employing an asymmetric waveform for filtering ions) should be located in the initial pumping stage of a mass spectrometer housing. Furthermore, one proposal is that particular pressure and waveform frequencies should be applied to the DMS device to achieve good resolving power and ion transmission. Furthermore, another proposal is that a multipole DMS device should be used and a dipole field should be used in combination with a higher order field applied to the multipole to achieve radial focusing of ions.

In a first aspect, the present invention provides an ion analysis apparatus comprising:
  an ionization source for generating ions from a sample; and
  an ion detector;
  wherein in use ions travel along an ion optical axis from the ionization source to the ion detector, the apparatus further comprising:
  a vacuum enclosure including
    a first vacuum region containing differential ion mobility means; and
    a second vacuum region containing a mass analyzer;
  pumping means configured to provide a pressure in the second vacuum region that is lower than the pressure in the first vacuum region;
  an ion inlet connecting the ionization source to the first vacuum region,
  wherein the first vacuum region is located before the second vacuum region on the ion optical axis such that in use ions generated from the sample undergo differential ion mobility analysis before mass analysis,
  and wherein in use the first vacuum region including the differential ion mobility means is at a pressure in the range 0.005 kPa to 40 kPa and the differential ion mobility means is driven by an asymmetric waveform having a frequency in the range 20 kHz to 25 MHz.

The term "ion optical axis" as used herein will be familiar to the skilled person and pertains to the path taken by ions during their transit through the apparatus. The ion path (ion optical axis) can be partly or entirely linear or partly or entirely curved.

As discussed below, in embodiments, the apparatus includes a waveform generator to generate the asymmetric waveform, i.e. configured to apply an asymmetric waveform to the differential ion mobility means, e.g. to at least one electrode of the differential ion mobility means. Preferred features of the waveform generator and the differential ion mobility means are discussed herein.

Operation of a DMS at the reduced pressures encountered in these regions of the MS (i.e. in the first vacuum region, also referred to herein as the DMS region) can extend the range of E/N values considerably compared to conventional DMS devices operated externally to the vacuum chamber, without the complication of having to transport ions through the inlet capillary or orifice of a MS vacuum interface by distorting gas flow.

In addition, as indicated by the Paschen curve discussed below, higher E/N values can be achieved at reduced pressure before initiating a breakdown.

Furthermore, the lower pressure means that the amplitude of the waveform can be reduced substantially, which allows the waveform to operate at much greater frequencies since power is proportional to voltage and frequency, $P \propto V^2 f$. Asymmetric waveforms operated at higher frequencies enhance transmission since the amplitude of oscillation of the ions, hence the number of ions discharging on the boundary electrodes, is minimized. Lower voltage and therefore lower power consumption becomes particularly beneficial when employing a rectangular asymmetric waveform, for example as generated by high-voltage high-frequency switches.

Another advantage of performing differential mobility separation of ions within the vacuum enclosure of a mass spectrometer is to make use of the high speed gas expansion of the gas released through the inlet orifice or capillary of the MS into the vacuum enclosure. It is then possible to shape the gas flow by appropriate means and suitably filter ions faster compared to the filtering performed at ambient or sub-ambient pressures.

A particular advantage of performing differential mobility spectrometry of ions in the first pumping stages of a mass spectrometer is to allow for complete desolvation of charged droplets and adduct ions, formed for example in an electrospray ionization (ESI) source, as they are transported through the heated inlet capillary of the MS. To those skilled in the art of ESI DMS or ESI FAIMS operated at- or near-ambient conditions, it is known that adduct ions transported through the DMS channel undergo dissociation as they enter the MS and can complicate the differential mobility spectra considerably reducing the effectiveness of the overall analysis.

A yet further advantage is that performing differential mobility separation in the vacuum enclosure of a MS prior to mass analysis practically eliminates the need for re-designing the ionization source and allows for existing external ion source configurations to be utilized.

The combination of the specified pressure and frequency ranges defined above have been found to provide particularly good results. The present inventors have found that these pressure and frequency ranges provide effective operating conditions for the differential ion mobility means as defined herein. In embodiments, both good resolving power and ion transmission can be achieved by selection of pressure and frequency within the specified ranges. In contrast, the present inventors have found that pressures and frequencies out side these ranges results in one or both of resolving power and ion transmission becoming unacceptable.

Embodiments described herein demonstrate the arrangement and configuration of a DMS device in the context of the mass analyzer-containing apparatus for optimum transmission of the filtered ions, combined with controllable resolving power. This makes the apparatus useful for a variety of applications. For example, in a high resolving power mode, a compensation voltage may be scanned resulting in a high quality spectrum of differential mobility. In another application a lower resolution may be employed to select for transmission one group of ions and exclude other groups of ions. For example, this can advantageously be applied to exclude solvent cluster ions. In the latter case the DMS can act to enhance the performance of the mass analyser. Thus, embodiments provide an apparatus comprising a mass analyser and a DMS device that is effective in the filtering or selecting of ions according to their differential mobility.

A particularly preferred pressure range is 0.01 kPa to 40 kPa, more preferably 0.01 kPa to 20 kPa (0.1 mbar to 200 mbar), more preferably 0.1 kPa to 20 kPa (1 mbar to 200 mbar), and most preferably 0.5 kPa to 5 kPa (5 mbar to 50 mbar).

Suitably the apparatus comprises pressure control means configured to provide the desired pressure. For example, such pressure control means may be the pumping means and/or gas flow means as described herein.

A particularly preferred frequency range is 0.5 MHz to 20 MHz, more preferably 0.1 MHz to 20 MHz, more preferably 0.25 MHz to 15 MHz, more preferably 0.3 MHz to 10 MHz, and most preferably 0.4 MHz to 8 MHz.

In embodiments, the apparatus includes a frequency controller and the frequency controller is configured to provide the frequency ranges referred to herein. Suitably the apparatus comprises a waveform generator, as discussed in more detail below, and preferably the waveform generator is configured to produce the frequency ranges referred to herein. In such cases, the waveform generator can perform the function of the frequency controller. In embodiments wherein a digital waveform (see below) is used, e.g. as provided by a digital waveform generator, the frequency can be controlled by the digital waveform generator.

The present inventors have noted that the electric field to number density of the gas medium (E/N) at which the DMS device can operate is limited by electrical breakdown limitation to approximately 100 Td, at atmospheric pressure. At the reduced pressures referred to herein the range can be extended, to, for example, 500 Td without risk of electrical breakdown. Such extension of (E/N) can be used to improve analytical performance, and/or it may be used to lower the applied voltage. Suitably this permits a reduction in the complexity, size and cost of the asymmetric waveform generator.

The present inventors have found that improved performance can be achieved by operating in specific frequency ranges of the asymmetric waveform and in specific pressure ranges. In particular, embodiments provide good analytical performance in combination with good transmission characteristics.

The pressure and frequency ranges defined herein have been derived by the present inventors from their studies of the resolving power and ion transmission at different pressures and frequencies. Extensive simulations carried out by the present inventors have resulted in an understanding of the "working region" of pressure and frequency which provides effective performance.

In particular, the present inventors have observed, from their simulations and modeling experiments, that there is a high frequency boundary that arises because of the time taken for a population of ions to reach a steady state drift velocity following a change in the asymmetric waveform, for example from high to low field conditions. It has been found that resolving power deteriorates markedly if the time taken to reach steady state drift velocity is long with respect to the time in which the waveform is in a particular state (e.g. a high or low field state). This gives rise to an upper limit on waveform frequency. In particular, it has been found that at frequencies above those specified herein, the resolving power is poor.

A lower frequency boundary or limit has also been deduced by the present inventors. It has been observed that if the frequency is too low, the amplitude of oscillation of the ion becomes too great and ion losses significant. In particular, at frequencies below those specified herein, ion transmission is poor.

As for the high pressure boundary, the present inventors have observed that in order to maintain the E/N value in a range that exploits advantages of vacuum DMS, namely the ion mobility K(E/N) being in the non-linear region, the applied voltage must be increased in proportion to pressure. Above a particular pressure, the voltage is high enough to cause voltage breakdown of the gas.

As regards the low pressure limit boundary, the present inventors have found that the gas flow must be sufficiently laminar for efficient transportation of ions through the DMS channel. In particular, at pressures below those specified herein, ion transmission is poor or non-existent.

These pressure and frequency boundaries together define a "working region". In embodiments operating within this working region, both good resolving power and ion transmission have been achieved.

Furthermore, in some cases, the present inventors have found that, for a given pressure, the effective range of frequencies is constrained, and vice versa.

Thus, a device that is operated with a given analytical gap, d, may be operated to select a particular ion from ions transmitted with a range of mobility values by changing the frequency of the asymmetric waveform, to move between different operating regions of low, medium and high mobility.

Suitably the frequency of the asymmetric waveform, for example a digitally driven waveform (see below), is changed in use. In particular, preferably the frequency is changed between different operating regions of low, medium and high mobility. Thus, in embodiments, the apparatus includes a waveform generator that is a variable waveform generator, suitably adapted or configured to change the waveform, suitably the frequency of the waveform, in use. Such embodiments provide greater flexibility than prior art devices, where an asymmetric waveform is generated by a fixed frequency generator.

In other embodiments, the frequency of the waveform is adjusted between experiments, for example to be tailored to a particular sample.

Typical values for the analytical gap, d, of the differential ion mobility means are in the range 1 mm to 25 mm, preferably 2 mm to 20 mm, and more preferably 5 mm to 15 mm.

The present inventors have observed that for different values of d, the pressure and/or frequency values can be tailored to optimize performance.

Suitably, for very small values of d, for example 1 mm to <2.5 mm, especially where d is about 2 mm, a pressure range of 0.7 kPa to 27 kPa and/or a frequency range of 0.3 MHz to 20 MHz is/are preferred. More preferably the ranges are 2 kPa to 10.5 kPa and/or 1.5 MHz to 5 MHz. A particularly effective pressure is about 5.9 kPa and a particularly effective frequency about 2.5 MHz.

Suitably, for small values of d, for example 2.5 mm to <7.5 mm, especially 4 mm to 6 mm, and especially where d is about 5 mm, a pressure range of 0.4 kPa to 13.2 kPa and/or a frequency range of 0.2 MHz to 10 MHz is/are preferred. More preferably the ranges are 0.5 kPa to 6.6 kPa and/or 0.6 MHz to 2.5 MHz. A particularly effective pressure is about 2.6 kPa and a particularly effective frequency about 1 MHz.

Suitably, for medium values of d, especially in the range 7.5 mm to <15 mm, especially 9 mm to 13 mm, especially 9 mm to 11 mm, and especially where d is about 10 mm, a pressure range of 0.2 kPa to 10.5 kPa and/or a frequency range of 0.05 MHz to 6 MHz is/are preferred. More preferably the ranges are 0.2 kPa to 4.6 kPa and/or 0.3 MHz to 1.5 MHz. A particularly effective pressure is about 1.3 kPa and a particularly effective frequency about 0.5 MHz.

Suitably, for large values of d, especially in the range 15 mm to ≤25 mm, especially 17 mm to 23 mm, especially 18 mm to 22 m, and especially where d is about 20 mm, a pressure range of 0.008 kPa to 6.6 kPa and/or a frequency range of 0.03 MHz to 5 MHz is/are preferred. More preferably the ranges are 0.008 kPa to 3.3 kPa and/or 0.15 MHz to 1 MHz. A particularly effective pressure is about 0.7 kPa and a particularly effective frequency about 0.3 MHz.

In embodiments, the pressure and frequency are selected from: (a) 0.7 kPa to 27 kPa and 0.3 MHz to 20 MHz; (b) 0.4 kPa to 13.2 kPa and 0.2 MHz to 10 MHz; (c) 0.2 kPa to 10.5 kPa and 0.05 MHz to 6 MHz; and (d) 0.008 kPa to 6.6 kPa and 0.03 MHz to 5 MHz.

In embodiments, the pressure and frequency are selected from: (a) 2 kPa to 10.5 kPa and 1.5 MHz to 5 MHz; (b) 0.5 kPa to 6.6 kPa and 0.6 MHz to 2.5 MHz; (c) 0.2 kPa to 4.6 kPa and 0.3 MHz to 1.5 MHz; and (d) 0.008 kPa to 3.3 kPa and 0.15 MHz to 1 MHz.

Preferably the asymmetric waveform applied to the differential ion mobility means is a digital waveform, i.e. the differential ion mobility means is provided with a digitally driven asymmetric waveform. In practice a high voltage (suitably a time-varying rectangular wave voltage) is applied to the differential ion mobility means in response to a low voltage signal waveform. References herein to applying or providing a digital waveform to the differential ion mobility means should therefore be understood to include applying or providing a high voltage that is generated in response to a signal waveform. A digital waveform (digitally driven waveform) and the resultant voltage is familiar to the skilled reader and is characterized in that the high voltage is switched between two voltage levels (high and low voltage levels), wherein the switching is provided by switching means, which are driven by the low voltage and current digital circuit control means. Suitably such low voltage signal is provided by Direct Digital Synthesis method (DDS).

WO02/50866, which is incorporated herein by reference, describes suitable digital drive methods and apparatus (for example in FIG. 1 of WO02/50866). It describes a high voltage switch circuit that comprises two switch blocks which are in series connection between a high voltage source and a low voltage source; the two switch blocks are controlled by the low voltage digital signal to be alternatively conducted or cut off, so as to enable the high voltage switch circuit to switch between the high voltage and the low voltage to generate a high voltage rectangular wave; controlled by the digital signal to be simultaneously conducted or cut off. Such a system provides the capability to adjust the operating frequency over a wide range. Whilst the apparatus disclosed in WO02/50866 is unrelated to the DMS-MS system of the present invention, the present inventors have surprisingly found that it can be particularly effective when applied to the low pressure DMS-MS device of the present invention operating within specific regions of pressure and frequency space. The digital drive method provides this flexibility, in particular cases where it is necessary to apply the transmitting and separating signals to common electrodes.

Suitably the apparatus includes a waveform generator adapted to create a digital control signal (digital waveform). Such a waveform generator is also referred to herein as a digital waveform generator. Suitably the apparatus includes voltage switching means for generating a time-varying rectangular wave in response to digital waveform. The voltage switching means can be part of the waveform generator (digital waveform generator).

Suitably the apparatus includes duty cycle varying means for varying the duty cycle of the rectangular wave voltage. In embodiments the duty cycle varying means is said waveform generator (digital waveform generator).

It has been found that provision of a digital waveform results in further improvements in performance. In particular, the combination of a digital waveform with the frequencies and reduced pressures specified herein has been found to give surprisingly good resolving power and ion transmission. A particular advantage of employing a digital drive method is improved flexibility of operation. For example, a greater range of frequencies is accessible.

Suitably the (digital) waveform generator is adapted to produce different (e.g. a range of) frequencies, i.e. the waveform generator is a variable frequency waveform generator such that, for example, the frequency of rectangular wave voltage generated in response to the waveform can be varied, suitably within the frequency ranges disclosed herein.

A further advantage of a digital drive is that very rapid (suitably substantially instantaneous) switching between different waveforms can be achieved. Examples of such switching are discussed herein.

A yet further advantage of a digital waveform is a flexible duty cycle, in particular the possibility of achieving a high duty cycle. A high duty cycle can provide a greater difference between the high and low field levels and, in combination with an extended E/N, the greater difference in mobility between high and low field cases can be exploited. Suitably the (digital) waveform generator is adapted to produce different (e.g. a range of) duty cycles. As explained above, suitably the duty cycle of a rectangular wave voltage generated in response to a low voltage digital waveform can be varied.

Suitably the apparatus includes waveform switching means to switch between a first waveform and a second waveform. For example, this may permit switching between a first waveform where there is transmission of ions with a wide range of mobilities and a second waveform where ions are separated according to their differential mobility. Typically, this is achieved by selecting a first waveform having a rectangular waveform and a second waveform having a square waveform.

In embodiments, the waveform switching means is the waveform generator. Thus, preferably the waveform generator is configured so that the waveform can be switched. For example, the waveform generator is switchable from a first waveform to a second waveform (which second waveform is different from the first waveform).

In a particularly preferred embodiment, the waveform is switchable between a first waveform that has a duty cycle of 50% and a second waveform that has a duty cycle that is not 50% (e.g. more than or less than 50%). Suitably this permits switching between an ion transmission mode and an ion separation mode.

Suitably the waveform generator is configured to change the duty cycle, preferably in the range 0.05 to 0.5, to effect separation of ions, particularly ions with different high field mobility.

As discussed in more detail herein, a further advantage of operating a digital drive method is the duty cycle flexibility of the asymmetric waveform, in combination with the extended (E/N). The extended range of E/N provides for greater difference in the mobility between the high and low field case. Such differences are only exploited when the duty cycle is large, i.e. the high duty cycle provides greater difference between the high and low field application.

Typically the apparatus includes gas flow means for establishing a flow of gas into the first vacuum region so as to provide a gas medium for the differential ion mobility means. The gas flow means is preferably part of the gas inlet system described herein. Suitably the gas flow is associated with ionization source. Accordingly, it is particularly preferred that the apparatus includes gas flow means for establishing a flow of gas from the ionization source through the ion inlet into the first vacuum region so as to provide a gas medium for the differential ion mobility means. Conveniently, this might be achieved by utilizing the gas flow from the ionization source. Thus, in embodiments, the ionization source comprises ionization source gas flow means which provide the said flow of gas.

In embodiments, the gas flow provided by the gas flow means carries the ions through the apparatus, particularly through the differential ion mobility means, along the ion optical axis.

The gas provided by the gas flow means can be the same as or different from the gas in the ionization source. Suitably it is different. The gases can have different compositions (e.g. different amounts of the same type of gas) or be different types of gas. In such embodiments, the gas flow means is preferably not associated with the ionization source.

Alternatively or additionally the apparatus includes ion transport electric field means which in use provide an electric field that urges the ions through the apparatus, especially through the differential ion mobility means. Suitably the said electric field is longitudinal, that is it is substantially aligned with the ion optical axis (i.e. in the direction of ion travel). A "segmented electrode" DMS of the type discussed herein (with a plurality of electrodes arranged sequentially in the longitudinal direction) may be used to provide the desired longitudinal electric field In embodiments, the said electric field is superposed on the differential ion mobility electric field provided by the differential ion mobility means.

Thus, in embodiments the differential ion mobility means is provided with an axial electric field for the purpose of driving ions through the DMS. The axial electric field may be established by various means that are known in the art of transport ions guides. For example, by the use of an auxiliary resistive, segmented or inclined rod set, or by resistive coating means of main rods, or by segmentation of main rods.

The use of an electric field to drive ions through the mobility cell has the advantage that the DMS can be operated in a stationary gas flow, or a small counter gas flow.

In embodiments the DMS device may be effectively decoupled from an atmospheric pressure interface region. In other embodiments it can used for sub-ambient pressure ion sources or intermediate pressure Maldi ion source.

This embodiment may be employed, for example, when it is desirable that the mass analyser accepts ions simultaneously in a wide m/z range with uniform efficiency with respect to the m/z value of the ions. Examples of such a mass analysers are an ion trap mass analyser, Time-of-Flight (ToF) and Trap-ToF analysers. Decoupling the DMS device from the ion inlet means that is it possible to use in the first vacuum region a device which is designed for delivering ions over a wide m/z values.

In this case when the DMS device is operated in a transmission mode, the mass analyser will analyse all ions. In this way, the DMS may be located in the vacuum compartment of a mass analyser and operated at a pressure that is optimal for DMS performance and in the absence of strong gas dynamic effects. This suitably avoids the complicated task of designing a DMS cell to operate in the presence of strong gas dynamic effects.

A further advantage is that ion focusing means as described herein may be operated at a pressure which is optimal for maximum ion transmission. A yet further advantage is that the alternative gas types may be introduced to the DMS independently of the gas employed in the ionization source (e.g. API) interface. As noted above, the ionization source can be located either externally to the vacuum enclosure or within the vacuum enclosure.

Any ionization source can be used. The ionization source can be an ambient pressure ionization source, an intermediate pressure ionization source or a vacuum ionization source.

In the case of ionization source being located externally to the vacuum chamber, suitably the ionization source is selected from electrospray ionization (ESI), desorption electrospray ionization (DESI), chemical ionization (CI), atmospheric pressure ionization (API), atmospheric pressure MALDI and Penning ionization.

In certain embodiments, the ionization source is located in an ionization source vacuum chamber in the vacuum enclosure. In such embodiments, the ionization source is a matrix assisted laser desorption ionization (MALDI) source, preferably an intermediate pressure MALDI source or high vacuum MALDI.

In embodiments, the ionization source vacuum chamber comprises a gas inlet, which gas inlet suitably provides the flow of gas to the first vacuum region as discussed herein.

Suitably the first vacuum region includes first and second compartments. That is, the first vacuum region in which DMS analysis occurs may be divided into two compartments. Typically each compartment is a conventional vacuum compartment and is pumped in the normal way. Ion transit between the compartments is suitably via an appropriate aperture or orifice (e.g. a skimmer) in the wall separating the compartments.

In some embodiments, there are more than two vacuum compartments in the first vacuum region, for example three or four.

The pressure in the first and second compartments can be substantially the same or different. Preferably the pressure in the first compartment is greater than the pressure in the second compartment. In such embodiments, it is preferred that the pumping means is configured to provide a pressure in the first compartment that is higher than the pressure in the second compartment. Suitably the pumping means allows the pressure in each of the first and second compartments to be adjusted independently.

Suitably the apparatus includes a gas inlet system to provide gas to the vacuum enclosure (e.g. to the first and/or second vacuum region; to the first and/or second vacuum compartment). Preferably the gas inlet system is configured to allow independent adjustment of the gas flow into the first and second compartments. It is particularly preferred that the pumping means and gas inlet means provide independent adjustment of pressure in the first and second compartments.

However, it is also possible to operate the apparatus with the first compartment at a lower pressure than the second compartment.

Where there the first vacuum region (the DMS region) comprises first and second vacuum compartments, the differential ion mobility means is preferably located in the first compartment.

In other arrangements, the differential ion mobility means is located in the second compartment.

In further embodiments, the differential ion mobility means has an ion entrance and an ion exit, wherein the differential ion mobility means is located such that the ion entrance is in the first compartment and the ion exit is in the second compartment. That is, suitably the differential ion mobility means extends into both vacuum compartments. This has the advantage that control of pressure in the first and second vacuum compartments can be used to adjust gas flow through the differential ion mobility means.

The first vacuum region (DMS region) can include components in addition to the differential ion mobility means. For example, ion optical focusing means can be located in the first vacuum region, suitably before or after the differential ion mobility means. Ion optical focusing means may be a multipole, ion funnel, or quadrupole array device.

In embodiments, the first vacuum region includes ion optical focusing means located before the differential ion mobility means.

In the case of the first vacuum region comprising first and second vacuum compartments, suitably the first compartment includes ion optical focusing means. Suitably, independently of the first vacuum compartment, the second compartment includes ion optical focusing means.

In embodiments, the second vacuum region (MS region) can include components in addition to the mass analyzer. For example the second vacuum region may include a collisional cooling cell, suitably located before the mass analyzer on the ion optical axis.

The second vacuum region (MS region) may comprise two or more vacuum compartments. In such arrangements, the mass analyzer is located in one of the vacuum compartments (the MS vacuum compartment). Suitably the mass analyzer is located in the last of the vacuum compartments (that is, the last vacuum compartment along the ion optical axis).

Preferably the apparatus includes, in the first vacuum region, gas flow modifying means associated with the ion inlet, which gas flow modifying means is configured to reduce the turbulence of gas flow into the first vacuum region. Suitably the gas flow modifying means is configured to provide in use a substantially laminar gas flow to the differential ion mobility means.

Suitably the ion inlet has an exit portion in the first vacuum region and the gas flow modifying means is connected to or adjacent the ion inlet exit portion and is spaced from the differential ion mobility means.

The skilled reader is able to select an appropriate shape for the gas flow modifying means and particularly preferred is a substantially conical member.

In embodiments, suitably the ion inlet is selected from a capillary and an orifice. In arrangements wherein the ionization source is located externally to the vacuum enclosure, the ion inlet provides an ion path from the exterior of the vacuum enclosure to the first vacuum region.

The differential ion mobility means can be any appropriate device known to the skilled person. Indeed, an advantage of the present invention is that a conventional DMS cell can be readily modified so as to operate within the first vacuum region. The performance of a DMS cell can be enhanced by altering the nature of collisions as pressure and voltage is reduced.

Suitably the differential ion mobility means (e.g. DMS cell) comprises an electrode arrangement selected from:
(a) two planar parallel electrodes;
(b) two concentric cylindrical electrodes; and
(c) a multipole wherein a plurality of elongate electrodes are arranged circumferentially around a common axis, with the longitudinal axes of the electrodes being parallel.

A multipole is particularly preferred. Suitably the common axis of the multipole is the ion optical axis. Suitably the electrodes are arranged symmetrically around the common axis. Suitably the multipole has a circular cross section. Suitably, each electrode of the multipole is curved to accommodate the circumferential arrangement.

Preferably the differential ion mobility means comprises a waveform generator as described herein, configured to apply an asymmetric waveform to at least one electrode of the multipole. In this way, an alternating electric field is established between the electrodes. As discussed above, it is preferred that the waveform generator is configured to apply a digital waveform to at least one electrode of the multipole (suitably a voltage in response to the waveform).

Suitably the apparatus includes dipole field means for generating a dipole field with the multipole.

It is preferred that the dipole field means is the waveform generator, such that the waveform generator is configured to provide a dipole field within the multipole (i.e. within the space defined by the electrodes of the multipole). In practice, as, discussed above, a voltage in response to the waveform is applied to the multipole.

It is further preferred that the waveform generator is configured to provide an additional field, suitably a higher order field (for example a quadrupole field), within the multipole. It is preferred that a higher order field is superimposed on the dipole field. Thus, suitably, a higher order field and dipole field are applied within the space defined by the electrodes of the multipole.

The multipole is suitably selected from a quadrupole (n=4), hexapole (n=6), octapole (n=8) and dodecapole (n=12). However, any value of n in the range of 4 to 12 is suitable.

A preferred embodiment of a multipole is a dodecapole (12-pole), for example as shown in the FIGS. 2 and 3.

A suitable (inscribed) radius is 1 mm to 10 mm (d=2 mm to 20 mm). A suitable length is 20 mm to 150 mm.

In a preferred embodiment such as the one shown in FIGS. 2 and 3, the (inscribed) radius is about 2.5 mm (d=5 mm) and the length is about 70 mm.

Suitably the apparatus includes additional voltage means that superimposes an additional voltage on to at least one of the electrodes of the differential ion mobility means (DMS) to effect focusing of selected ions in the radial direction towards the central longitudinal axis of the DMS, Thus, radial confinement can be achieved.

Preferably the additional voltage means provides an additional field within the multipole such that the additional field effects radial focusing of the ions. Suitably the additional voltage is controlled by a waveform generator as disclosed herein. For example, the signal produced by the waveform generator is used to control the voltage applied to the DMS, In embodiments, a common voltage source is used to apply the "normal" DMS voltage and the additional voltage.

Suitably the apparatus, preferably the waveform generator, is configured to provide a (i) dipole field and (ii) a higher order field within the multipole. Suitably the higher order field is a quadrupole (n=4) or higher field. In embodiments the higher order field is selected from n=4 to 12. The upper limit on the order is the number of electrodes, such that n is less than or equal to the number of electrodes.

Typically the higher order field and the dipole field are applied simultaneously, suitably at the same waveform frequency and duty cycle. Suitably the higher order field is superimposed on the dipole field. However, in embodiments, the higher order field can be switched off independently of the dipole field such that only the dipole field is applied. For example, this might be used to achieve selective radial focusing of only certain ions and/or to permit the multipole to be operated in a non-focusing mode.

In embodiments, the multipole is switchable between focusing and non-focusing modes of operation (i.e. high order field on and higher order field off). Suitably this can be achieved by a waveform generator that is switchable between focusing and non-focusing modes.

Preferably, the higher order field comprises an (asymmetric) RF component and a DC component.

In embodiments, the DC signal is provided by a DC power supply, which is typically a separate power supply from the power supply for the RF signal.

More generally, preferably the differential ion mobility means can be switched off (no potential applied to the electrodes) independently of the rest of the apparatus, particularly independently of the mass analyzer. Suitably this would permit the apparatus to be used as a conventional mass spectrometer.

In embodiments, the differential ion mobility means comprises a plurality of electrodes arranged in the longitudinal direction. This sort of "segmented electrode" permits ion transport through the DMS by action of an electric field (additionally or alternatively to gas flow) as discussed herein.

Suitably the apparatus includes compensation voltage means, which in use applies a compensation voltage to at least one electrode of the differential ion mobility means.

Typically, the apparatus includes control means for operating the differential ion mobility means, suitably for controlling the waveform generator.

Preferably the pumping means includes at least one vacuum pump connected to the first vacuum region and at least one vacuum pump connected to the second vacuum region. Suitably, in order to achieve the low pressures required in the MS vacuum region, a turbomolecular pump is connected to the MS vacuum region.

Preferably the pumping means includes, for at least some of the vacuum pumps, a restriction located between the vacuum pump and the vacuum region. In embodiments, each restriction independently comprises a valve.

Suitably the pumping means and/or gas flow means (e.g. gas flow from the ionization source) are configured to provide the pressures in the first vacuum region referred to herein. Preferably the pumping means and ionization source are configured to provide a pressure in the first vacuum region of 0.005 kPa to 40 kPa (0.05 mbar to 400 mbar), preferably 0.1 kPa to 20 kPa (1 mbar to 200 mbar).

Preferably the pumping means and ionization source are configured to provide a pressure in the second vacuum region of less than $10^{-4}$ kPa ($10^{-3}$ mbar).

Preferably the first vacuum region is connected to the second vacuum region only by a single orifice.

Any mass analyzer can be employed, which mass analyzer can be selected by the skilled reader. Preferably the mass analyzer is selected from a quadrupole filter, time of flight analyzer (TOF), linear RF ion trap and electrostatic ion trap.

Suitably the apparatus is a mass spectrometer, preferably a TOF mass spectrometer.

Whilst the second vacuum region may comprise more than one mass analyzer, it is preferred that the apparatus includes only a single mass analyzer.

In other embodiments, the apparatus comprises a hybrid or tandem MS. In particular, the apparatus preferably includes, after the said mass analyzer, a further mass analyzer. Such arrangements can be configured so that the first mass analyzer selects ions of interest, which selected ions may then fragmented, with the resultant fragment or daughter ions being analyzed by the second mass analyzer.

In a further aspect, the present invention provides a mass spectrometer comprising
- an ionization source,
- a vacuum enclosure having first and second vacuum regions, the first vacuum region comprising an ion inlet through which ions from the ionization source are introduced into the first vacuum region,
- differential ion mobility means located in the first vacuum region, and
- a mass analyzer located in the second vacuum region, such that in use ions travel along an ion optical from the ionization source through the first vacuum region to the mass analyzer, such that in use ions generated from the sample undergo differential ion mobility analysis before mass analysis,
- and wherein in use the first vacuum region including the differential ion mobility means is at a pressure in the range 0.005 kPa to 40 kPa and the differential ion mobility means is driven by an asymmetric waveform having a frequency in the range 20 kHz to 25 MHz.

The optional and preferred features associated with the first aspect also apply to this aspect.

In a further aspect, the present invention provides a method of using the apparatus and spectrometer described herein to analyze ions.

In a further aspect, the present invention provides a method of analyzing ions, which method comprises the steps of:
(a) generating ions from a sample in an ionization source;
(b) delivering the ions through an ion inlet into a first vacuum region of a vacuum enclosure;
(c) in the first vacuum region, prior to mass analysis of the ions, conducting differential ion mobility analysis of the ions;
(d) after differential ion mobility analysis, delivering the ions to a second vacuum region of the vacuum enclosure; and
(e) in the second vacuum region conducting mass analysis of the ions;
wherein step (c) includes applying an asymmetric waveform having a frequency in the range 20 kHz to 25 MHz to the ions, and wherein step (c) is conducted at a pressure in the range 0.005 kPa to 40 kPa.

Thus, in the method of this aspect, the ions produced from the ionization source are conveyed to a first region of the vacuum enclosure of the apparatus where they are subjected to DMS analysis under the specified conditions, followed by transit to a second region of the vacuum enclosure where they undergo mass analysis.

Preferably step (b) includes providing a flow of gas from said ion source into said first vacuum region such that the differential ion mobility analysis occurs in the gas.

Suitably the flow of gas is modified in the first vacuum region to reduce the turbulence of the flow of gas prior to differential ion mobility analysis. Preferably differential ion mobility analysis occurs in a substantially laminar flow of gas.

Alternatively or additionally, and as discussed above, the ions may be transported through the differential ion mobility means by operation of an electric field (suitably a longitudinal electric field). In such arrangements, preferably there is substantially no gas flow through the differential ion mobility means (for example a static gas environment).

In embodiments, the ions are focused prior to and/or after differential ion mobility analysis.

As discussed herein, suitably ion differential analysis occurs at a pressure of 0.01 kPa to 40 kPa (0.1 mbar to 400 mbar), preferably 0.1 kPa to 20 kPa (1 mbar to 200 mbar).

As also discussed herein, preferably mass analysis occurs at a pressure of less than $10^{-4}$ kPa ($10^{-3}$ mbar).

The optional and preferred features associated with the first aspect also apply to this aspect.

In a further aspect, the present invention provides an ion analysis apparatus comprising:
- an ionization source for generating ions from a sample; and
- an ion detector;
- wherein in use ions travel along an ion optical axis from the ionization source to the ion detector, the apparatus further comprising:

a vacuum enclosure including
a first vacuum region containing differential ion mobility means; and
a second vacuum region containing a mass analyzer;
pumping means configured to provide a pressure in the second vacuum region that is lower than the pressure in the first vacuum region;
an ion inlet connecting the ionization source to the first vacuum region,
the first vacuum region being located before the second vacuum region on the ion optical axis such that in use ions generated from the sample undergo differential ion mobility analysis before mass analysis,
wherein the differential ion mobility means comprises a multipole wherein a plurality of elongate electrodes are arranged circumferentially around a common axis, with the longitudinal axes of the electrodes being parallel,
and wherein the apparatus includes a waveform generator configured to provide (i) a dipole field and (ii) a higher order field within the multipole.

As described herein, this arrangement has been found to provide radial focusing of the ions.

Suitably the common axis is the ion optical axis.

Typically the higher order field and the dipole field are applied simultaneously within the multipole. Suitably the higher order field is superimposed on the dipole field. For example, a higher order field can be applied within the space defined by the electrodes of the multipole.

Preferably the higher order field is a quadrupole field.

Suitably, the optional and preferred features of any one of the other aspects apply to this aspect. In particular, the discussion in the first aspect of the multipole and the fields and voltages applied to the multipole also applies to this aspect.

In a further aspect, the present invention provides a method of analyzing ions, which method comprises the steps of:
(a) generating ions from a sample in an ionization source;
(b) delivering the ions through an ion inlet into a first vacuum region of a vacuum enclosure;
(c) in the first vacuum region, prior to mass analysis of the ions, conducting differential ion mobility analysis of the ions;
(d) after differential ion mobility analysis, delivering the ions to a second vacuum enclosure; and
(e) in the second vacuum region conducting mass analysis of the ions;
wherein step (c) includes conducting differential ion mobility analysis with a multipole comprising a plurality of elongate electrodes arranged circumferentially around a common axis, with the longitudinal axes of the electrodes being parallel, and wherein step (c) includes applying (i) a dipole field and (ii) a higher order field within the multipole.

Suitably, the optional and preferred features of any one of the other aspects apply to this aspect. In particular, the discussion in the first aspect of the multipole and the fields and voltages applied to the multipole also applies to this aspect.

In a further aspect, the present invention provides an ion analysis apparatus comprising:
an ionization source for generating ions from a sample; and
an ion detector;
wherein in use ions travel along an ion optical axis from the ionization source to the ion detector, the apparatus further comprising:
a vacuum enclosure including
a first vacuum region containing differential ion mobility means; and
a second vacuum region containing a mass analyzer;
pumping means configured to provide a pressure in the second vacuum region that is lower than the pressure in the first vacuum region;
an ion inlet connecting the ionization source to the first vacuum region,
wherein the first vacuum region is located before the second vacuum region on the ion optical axis such that in use ions generated from the sample undergo differential ion mobility analysis before mass analysis.

The advantages of such an arrangement are discussed above in respect of the first aspect.

Suitably, the optional and preferred features of any one of the other aspects apply to this aspect.

In a further aspect, the present invention provides a method of analyzing ions, which method comprises the steps of:
(a) generating ions from a sample in an ionization source;
(b) delivering the ions through an ion inlet into a first vacuum region of a vacuum enclosure;
(c) in the first vacuum region, prior to mass analysis of the ions, conducting differential ion mobility analysis of the ions;
(d) after differential ion mobility analysis, delivering the ions to a second vacuum region of the vacuum enclosure; and
(e) in the second vacuum region conducting mass analysis of the ions.

Suitably, the optional and preferred features of any one of the other aspects apply to this aspect.

In a further aspect, the present invention provides a differential ion mobility cell (DMS cell) comprising a plurality of electrodes arranged sequentially in the direction of ion travel. Typically the DMS cell is elongate and the direction of ion travel corresponds to the longitudinal axis of the cell. It is therefore preferred that the plurality of electrodes are arranged sequentially in the direction of the longitudinal axis. Suitably the DMS cell includes ion transport electric field means which in use provide a voltage to the said plurality of electrodes so as to produce an electric field that urges the ions through the DMS cell.

This sort of "segmented electrode" permits ion transport through the DMS by action of an electric field (additionally or alternatively to gas flow) as discussed herein.

In a further aspect, the present invention provides a differential ion mobility cell (DMS cell) comprising a plurality of electrodes and ion transport electric field means which in use provides a voltage to the said plurality of electrodes so as to produce an electric field that urges the ions through the DMS cell.

A further related aspect provides an ion analysis spectrometer comprising a DMS cell as described herein. Suitably the spectrometer is a mass spectrometer and the DMS cell is located in a vacuum compartment of the mass spectrometer.

Any one of the aspects of the present invention may be combined with any one or more of the other aspects. Furthermore, any of the optional or preferred features of any one of the aspects may apply to any of the other aspects.

In particular, optional features associated with a method or use may apply to a product, and vice versa.

BRIEF DESCRIPTION OF THE DRAWINGS

Embodiments of the invention and information illustrating the advantages and/or implementation of the invention are described below, by way of example only, with respect to the accompanying drawings in which:

FIGS. 12*a* and 12*b* show a dodecapole DMS cell and the voltages applied to each electrode; 12*a* shows the dipole field (RF or DC) and 12*b* shows the quadrupole field (RF or DC); and FIGS. 13*a* and 13*b* are DMS spectra obtained with a combination of dipole and quadrupole fields.

DETAILED DESCRIPTION OF EMBODIMENTS AND EXPERIMENTS

Figure 1:
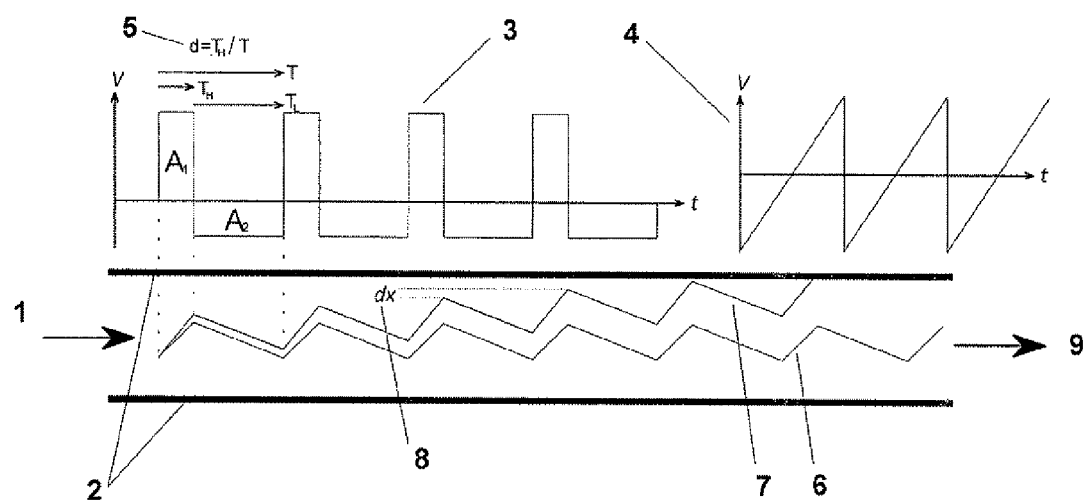
FIG. 1 shows a schematic diagram of a simplified DMS geometry illustrating ion motion dictated by variations of an asymmetric periodic waveform, including "sawtooth" compensation voltage.

Referring to FIG. 1, shown are basic principles and the mechanism for DMS separation based on the non-linear ion mobility dependence on electric field and pressure. Ions are entrained in a gas stream 1 established between two electrodes 2. The high frequency asymmetric waveform 3 is applied to one of the two electrodes. Superimposed to the waveform is a slow compensation dc voltage 4. The frequency of the asymmetric waveform usually spans between a few hundreds of KHz to ~1 MHz, while that of the "sawtooth" DC ramp 4 is <1 Hz. The amplitude of the asymmetric waveform when the DMS is operated at ambient pressure is limited by the breakdown limit of the gas flowing within a given electrode geometry and for a parallel plate DMS system the electric field does not generally exceed 3 KV mm$^{-1}$.

Still referring to FIG. 1, separation of ions is possible using waveforms substantially different than the pure rectangular waveform. A family of waveforms based on quasi-sinusoidal variations of the voltage as a function of time are widely used; these are the bi-sinusoidal, the clipped sinusoidal or other substantially rectangular waveforms. Asymmetric waveforms are designed so that the area of the positive pulse matches that of the negative pulse, $A_1=A_2$, For this particular arrangement of time-dependent electric fields, an ion with no mobility dependence on variations in electric field and pressure will therefore be transmitted at zero compensation voltage. The waveform is characterized by its duty cycle 5, usually defined as the width of the short positive pulse $T_H$ over the waveform period T. There exist optimum duty cycles for separating certain types of ions. For example the type A and C ions are best separated in the DMS spectrum when the duty cycle is ~0.33. B type ions exhibit a more complex behavior and having the ability to vary the duty cycle during the course of an experiment is essential for enhancing instrument performance.

Also shown in FIG. 1 are a stable ion trajectory 6 transmitted successfully through the system and a second ion trajectory hitting the top DMS electrode 7. Successful transportation of the lost ion 7 would require the appropriate compensation voltage to be applied to the DMS electrode to compensate for the small average displacement dx 8 introduced per waveform cycle. By scanning the compensation voltage, ions with different non-linear mobility dependencies on electric field and pressure are successively transported through the DMS gap and can either be collected on a plate connected to an electrometer, or monitored by a mass spectrometer 9 (not shown).

Figure 2:
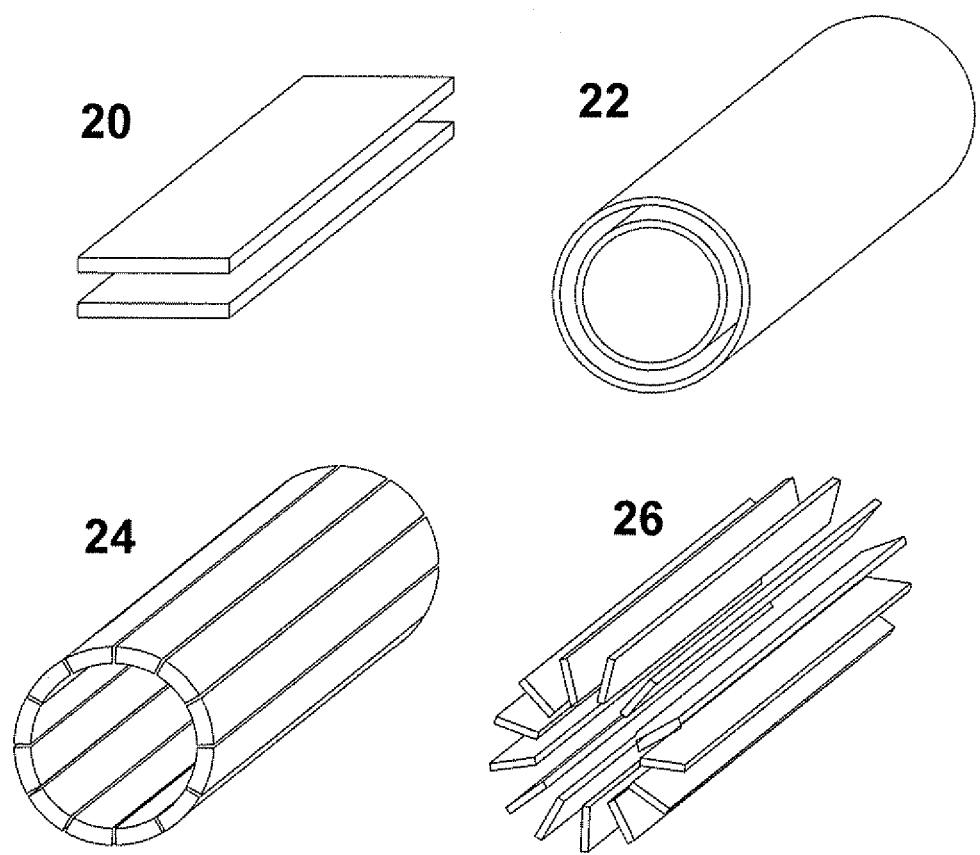
FIG. 2 shows electrode arrangements for performing differential mobility spectrometry.
Figure 3:
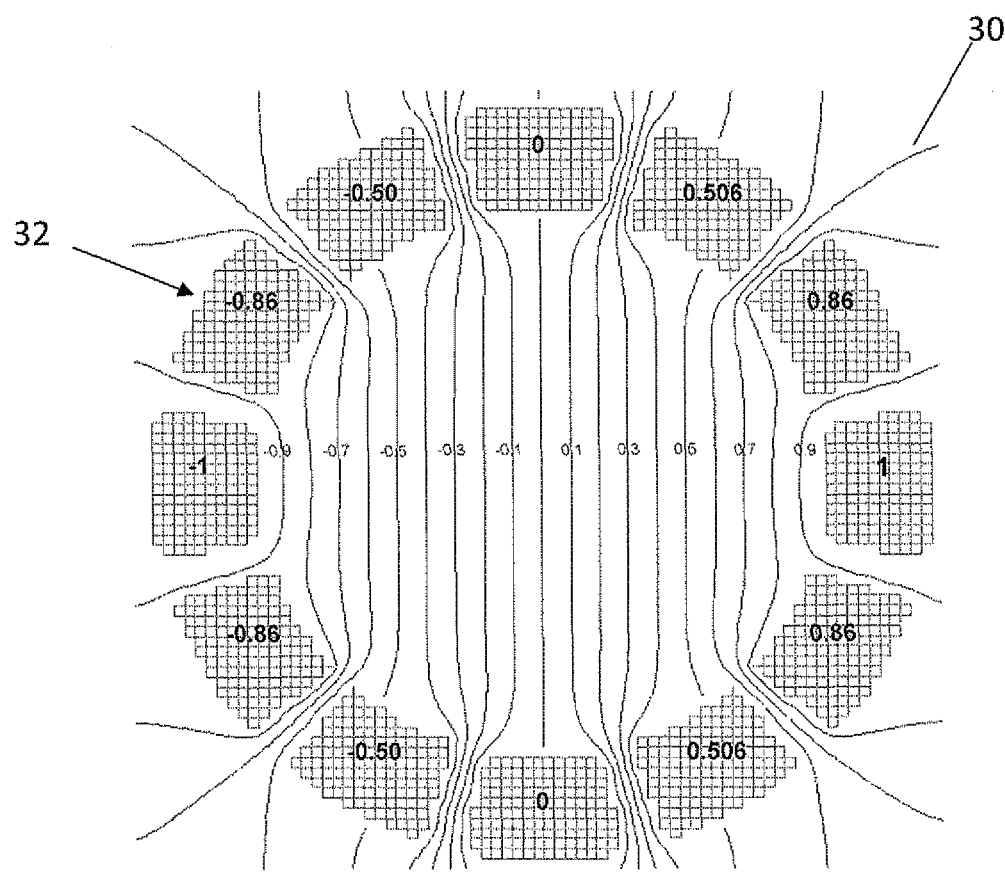
FIG. 3 shows a dodecapole arrangement of electrodes and normalized voltages and equipotentials for a dipole field.

FIG. 2 illustrates several possible electrode configurations for constructing a DMS device. The most commonly used configurations are the planar or parallel-plate system 20 and the axial arrangement of two concentric cylinders with different radii 22. Other configurations involve multipole systems of electrodes arranged coaxially about a central axis. In this example two different dodecapole geometries are shown, 24 and 26. A dipole field can be generated using such multipoles by applying a voltage V to each electrode according to the relationship $V=V_o \cos(n\theta/2)$, where n is the order of the field where in the case of a dipole n=2, θ is the angle of the electrodes as they are arranged about the axis of the system and $V_o$ is the input voltage, which defines the strength of the dipole field for a given inscribed radius. A normalized dipole field together with equipotential lines 30 for a dodecapole system 32 is shown in FIG. 3. Higher-order fields can be introduced using the same equation, for example, a quadrupole field (n=4) can be superimposed to the dipole field to provide focusing, similarly to the case of a cylindrical FAIMS arrangement.

Figure 4:
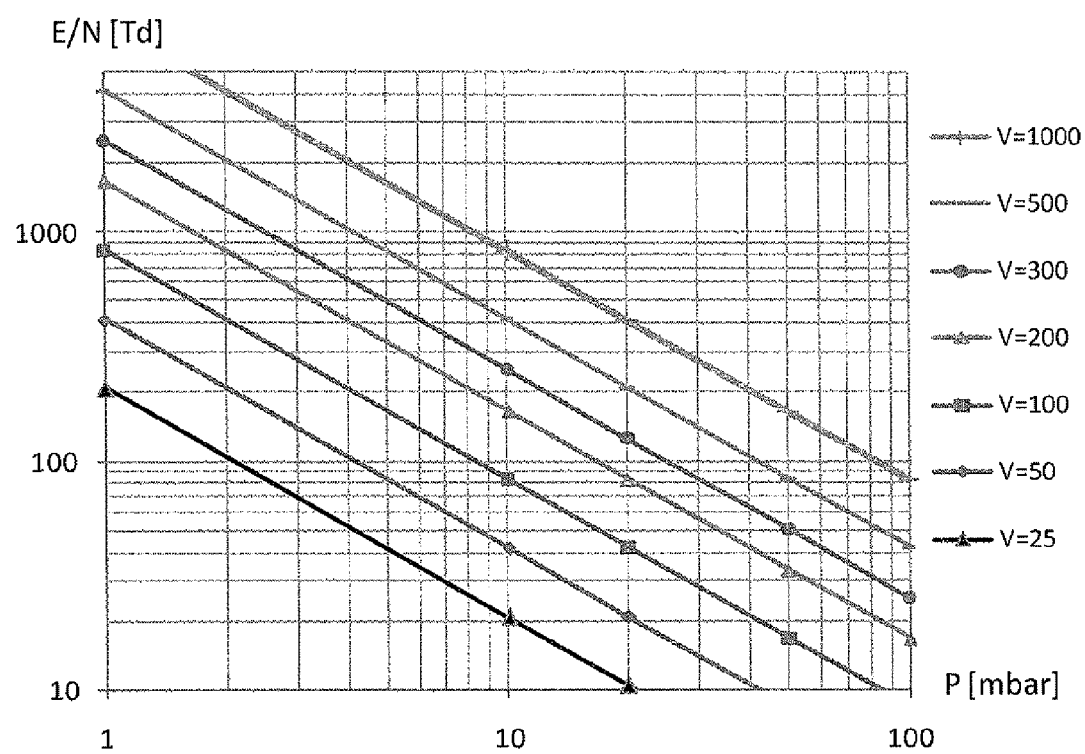
FIG. 4 shows a logarithmic plot of E/N in units of Td vs pressure in units of mbar.

FIG. 4 shows the range of the values for E/N for a 5 mm separation distance between two parallel plate-electrodes as the pressure is reduced for a pressure range of 1-100 mbar. For example, at a pressure of 1 mbar, and for 25 V across 5 mm, the value of E/N is ~200 Td, well above those achieved at ambient pressure. As mentioned above, the power consumption is significantly lower and, much higher frequencies can be used, enhancing transmission through the DMS channel. The Paschen curve predicts an upper limit of ~125 V for a spacing of 5 mm at ~1 mbar for breakdown to occur, The corresponding value for E/N is ~1000 Td.

Figure 5:
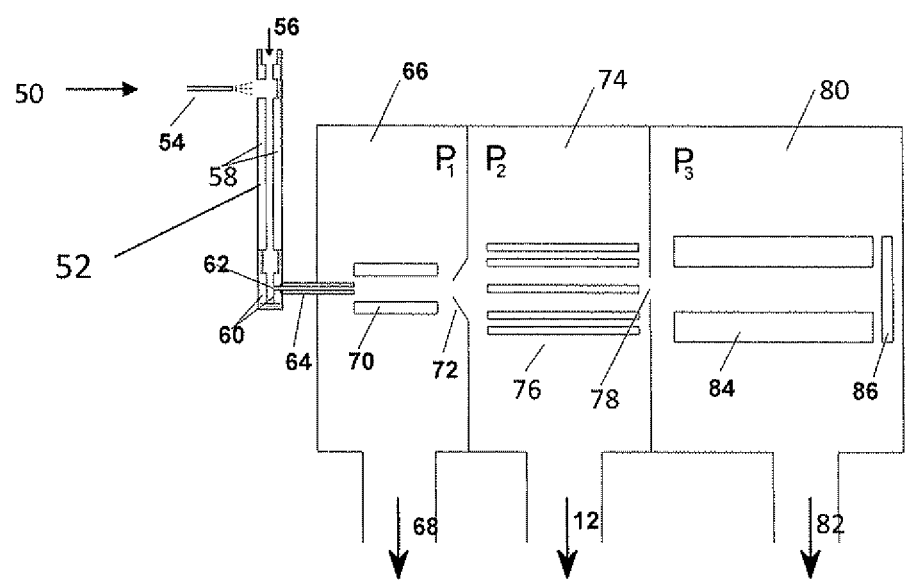
FIG. 5 shows a DMS-MS of the prior art attached externally to the vacuum enclosure of a mass spectrometer.

FIG. 5 shows a prior art apparatus 50 where a planar DMS 52 is attached externally to the front end of a mass spectrometer. Ions are electrosprayed 54 at the front end of the DMS and carried by gas flow 56 through the DMS channel where the high frequency asymmetric waveform and a slow sawtooth compensation voltage are applied to the planar electrodes 58. Two detector-plates 60 are situated to the rear end of the DMS for monitoring ion current transmitted through the device. A circular aperture 62 on one of the detector-plates allows for the ions to enter the MS through an inlet capillary 64, which also provides the necessary slow pumping of the gas through the DMS channel. A typical flow rate for an inlet capillary at the MS vacuum interface is ~1 L min$^{-1}$, which pre-defines the residence time of the gas in the DMS. Ions enter the first pumping stage 66 of the MS maintained at pressure $P_1$ by a vacuum pump 68 and are guided by an intermediate pressure RF lens 70 through a skimmer or an aperture 72 into the second vacuum chamber 74 maintained at a lower pressure $P_2$ by a turbo-molecular pump. Further cooling is introduced by collisions with the gas molecules as the ions traverse the multipole device 76 and focused through a final aperture 78 into the mass analyzer chamber 80 maintained at high vacuum conditions by an additional vacuum pump 82. Mass analysis in this example is performed using a quadrupole mass filter 84 and a mass spectrum is generated by monitoring ions by a detector, usually an electron multiplier 86.

Figure 6:
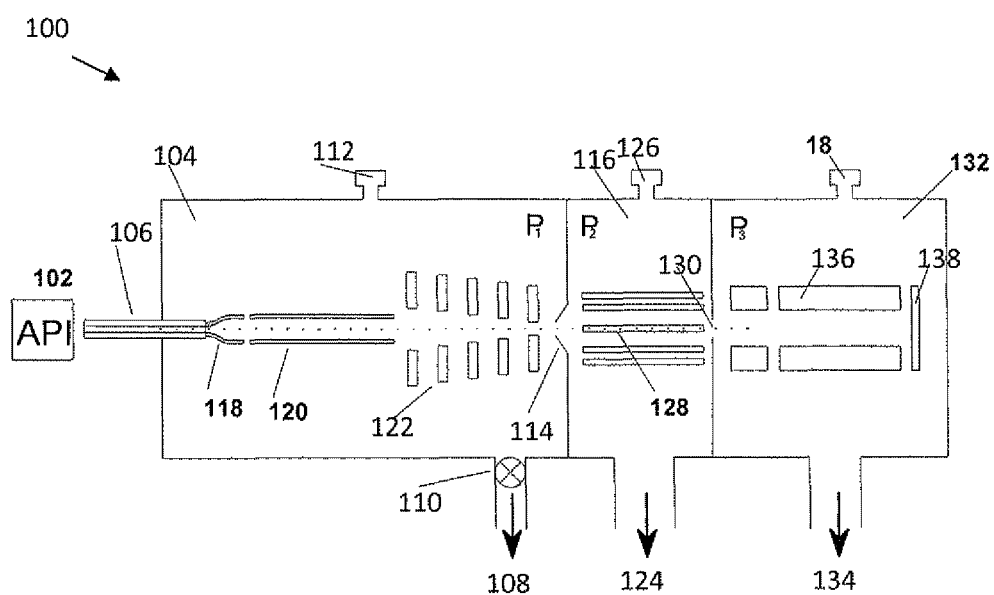
FIG. 6 is a schematic diagram of a preferred embodiment of the present invention wherein the DMS device is installed in the first pumping stage of the MS.

A preferred embodiment of the present invention where a DMS is installed in the first pumping stage of a mass spectrometer is illustrated in the schematic diagram of FIG. 6. In the illustrated DMS-MS apparatus 100, ions are generated in the atmospheric ionization (API) source region 102 and introduced into the first pumping stage of the instrument 104 through the inlet capillary 106. The pressure $P_1$ in the first vacuum chamber of the instrument is maintained by a rotary pump 108 and restriction 110 at pressures ~1 mbar, as indicated by a tubulated pressure gauge 112. Pumping is also provided through the skimmer or aperture 114 connecting the first 104 and second 116 vacuum chambers. Pressure in chamber 104 is controlled by the restriction 110 installed in the pumping line connected to rotary pump 108.

Ions and ambient gas, preferably purified $N_2$ used to provide the supporting atmosphere in the ionization source region 102, are introduced at a flow rate of ~1 Lmin$^{-1}$, which is a typical value for the pumping speed of an inlet capillary with an inner diameter of 0.5 mm and a length of ~10 mm. In the particular case of an electrospray ionization source, desolvation of droplets and adduct ions is provided by operating the inlet capillary at increased temperatures ranging from ambient conditions to 250° C. On entering the vacuum, ions and neutral particles form a jet and a conical- or bell-shaped lens 118 is used for shaping and directing the gas flow into a set of elongated electrodes comprising the DMS device 120. Ion losses encountered in the area a few mm past the entrance to the vacuum chamber where a standing barrel shock wave is formed by the supersonic jet expanding in vacuum can be minimized by directing and partially confining the gas flow through the electrodes of the DMS 120. Substantially laminar flow conditions can be established to transport the ions through the DMS and guiding those ions toward the subsequent ion optical focusing element 122.

The first vacuum chamber is pumped to a certain extent through the DMS electrodes 120, which allows to control the gas flow by the restriction valve 110. The ion optical focusing element 122, which can be an ion funnel or a q-array type device, receives ions spread over a broad area and confines ion motion delivering a confined ion beam to enter through the skimmer or aperture 114 into the second vacuum chamber 116 maintained at a lower pressure $P_2$ by a turbo-molecular pump 124, as measured by a second tubulated gauge 126. An octapole or any other multipole device 128 operated at pressures of ~10$^{-3}$ mbar is used for collisional cooling and further focusing the ion beam through an aperture 130 into the third vacuum chamber 132 connected to an additional vacuum pump 134 and accommodating the mass analyzer 136, and means for detecting mass analyzed ions 138.

Figure 7:
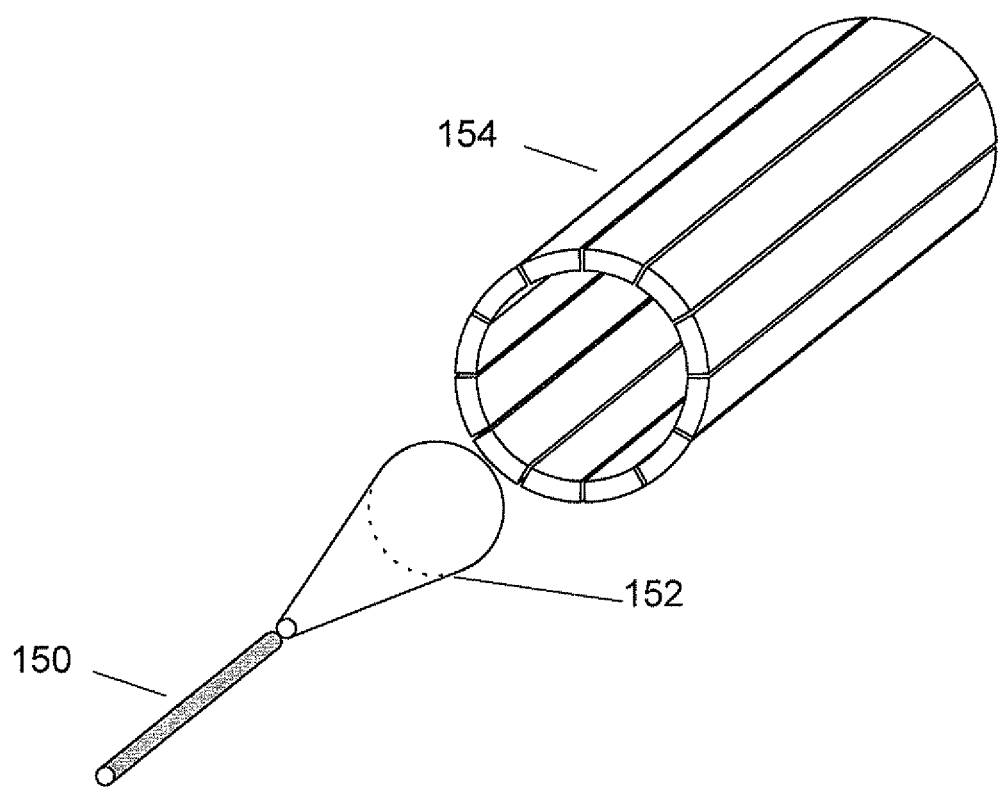
FIG. 7 is a schematic diagram of a conical gas shaper for establishing appropriate gas flow conditions through a dodecapole DMS arrangement.

FIG. 7 shows a simplified schematic diagram of an inlet capillary 150 and a conical-shaped element 152 for confining the shock wave and directing the gas toward a dodecapole DMS device 154. A smooth transition of the gas entering the vacuum is achieved by matching the entrance diameter of the conical gas flow shaper to that of the inlet capillary and the exit diameter to that of the cylindrical dodecapole.

Figure 8:
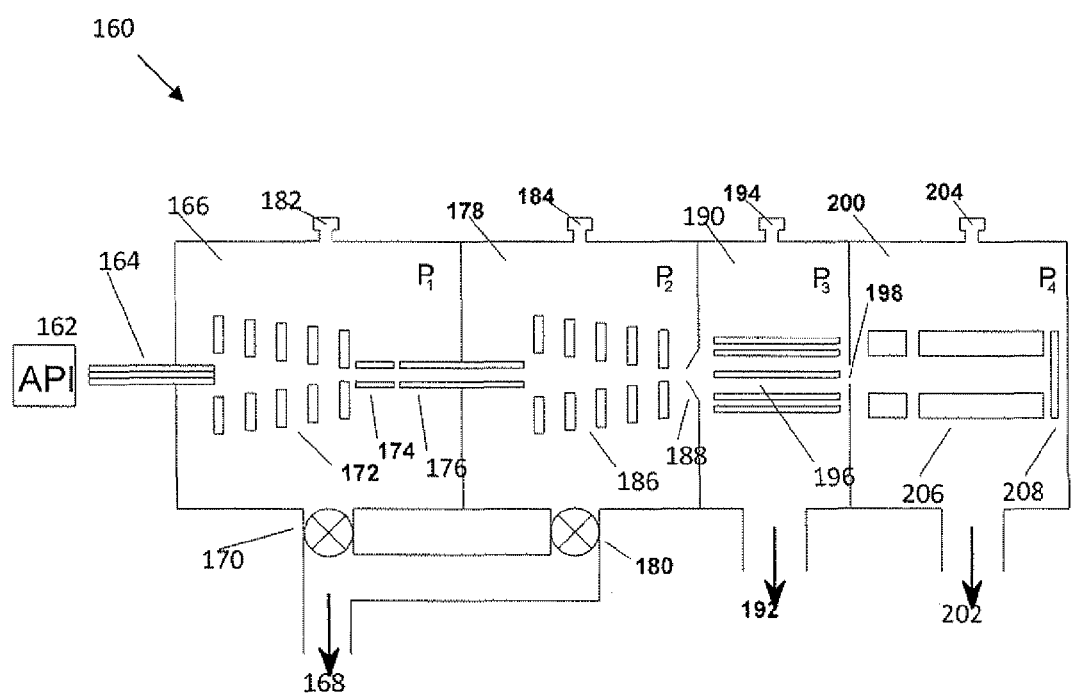
FIG. 8 is a schematic diagram of another preferred embodiment of the present invention wherein the DMS device extends between first and second vacuum compartments of the MS.

FIG. 8 shows yet another preferred embodiment, being an apparatus 160 comprising a DMS device accommodated in the vacuum chamber of a mass spectrometer. In this example ions generated in the API source 162 are sampled by the inlet capillary 164 and introduced to the first pumping stage 166 of the MS maintained at pressure $P_1$ by a vacuum pump 168 pumping through a restriction 170. Ions enter an ion funnel type device 172 and guided by an additional lens 174 into the DMS 176. The DMS electrodes extend between the first vacuum stage 172 and the second vacuum stage 178 maintained at a pressure $P_2$ lower than pressure $P_1$ by a vacuum pump. In this preferred embodiment, the same vacuum pump 168 through a second restriction 180 pumps both chambers. By adjusting restrictions 168 and 180, and monitoring pressures using pressure gauges 182 and 184, the pressure differential $P_1$-$P_2$ can be optimized for transporting ions through the DMS channel using gas flow. Filtered ions are then guided by a second ion funnel type device 186 and through the skimmer or aperture 188 into the consecutive third vacuum chamber 190 maintained at pressure of $P_3$ by a turbo-molecular pump 192. The pressure in the chamber is monitored by a pressure gauge 194 and ions are collisionally cooled in the octapole 196 and focused through an aperture 198 into the mass analyzer chamber 200 maintained at high vacuum pressure $P_4$ by a turbo-molecular pump 202. In this example, pressure is monitored by a hot cathode gauge 204, ions are mass analyzed by a mass filter 206 and collected by a detector 208.

Figure 9:
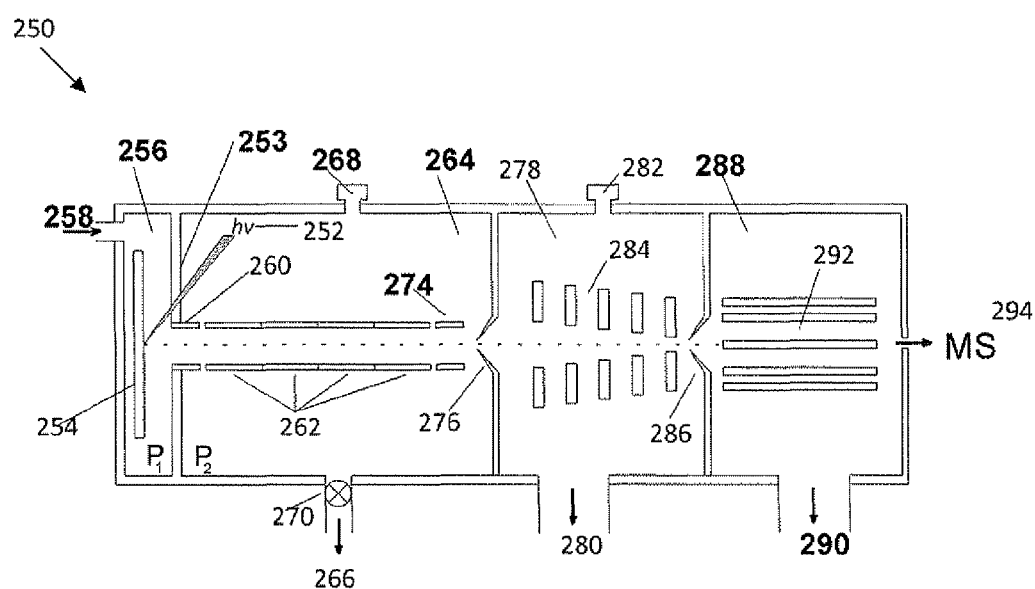
FIG. 9 is a schematic diagram of yet another preferred embodiment of the present invention wherein the DMS device is in a first pumping stage of the MS and the ionization source is accommodated in an ionization source vacuum chamber integral with the vacuum enclosure of the MS.

FIG. 9 shows yet another preferred embodiment, being an apparatus 250 comprising a DMS operated at reduced pressures and accommodated in the initial pumping stage of a mass spectrometer. Ions are generated by laser desorption ionization, preferably matrix-assisted laser desorption ionization (MALDI) source, where a pulse of laser light 252 is directed through a window 253 onto a target plate 254 carrying the sample to be analyzed. The sample plate 254 is enclosed in a small vacuum compartment 256 where gas is admitted through gas inlet 258 at the rear end to establish a pressure $P_1$.

Ions are focused by a lens 260 into the DMS 262 situated in a second vacuum compartment 264 maintained at pressure $P_2$ by a vacuum pump 266. Pressure is monitored by a pressure gauge 268 and can be adjusted by controlling gas flow rate through the inlet 258 and the restriction 270 imposed on the pump 266. Gas can be forced to flow from first to second vacuum compartment by increasing pressure $P_1$ relative to $P_2$. Ions are transported through the DMS channel either by gas flow or by a weak longitudinal electric field established by segmenting the DMS electrodes 272 and applying a dc-offset to each of the DMS electrodes separately. The additional weak dc-field superimposed to the asymmetric waveform may also separate ions along the axial direction. Ions are passed through a lens 274 and a skimmer 276 into the consecutive second vacuum chamber 278 maintained at low pressure by a vacuum pump 280 while pressure is monitored by a gauge 282. An ion funnel 284 focuses ions through a second skimmer or aperture 286 into another vacuum compartment 288 maintained at lower pressure by a vacuum pump 290 where ions are cooled as they travel through an ion guide 292 and finally focused through an aperture into the mass analyzer chamber 294.

Figure 10:
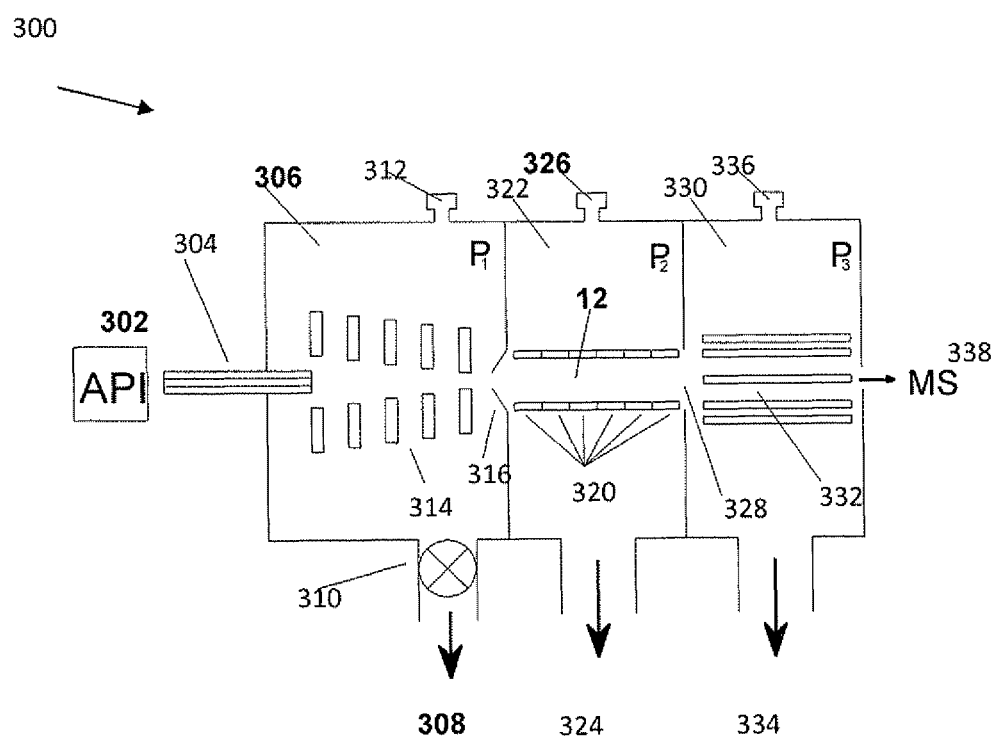
FIG. 10 is a schematic diagram of a yet further embodiment, wherein the DMS cell is in a second pumping stage of the MS and the ionization source is connected to the capillary inlet of the MS.

FIG. 10 shows yet another preferred embodiment, being an apparatus 300 comprising a DMS accommodated in the vacuum chamber of a mass spectrometer. Ions generated in a API source 302 are sampled by an inlet capillary 304 into the first pumping stage of a mass spectrometer 306 maintained by a vacuum pump 308 at pressure $P_1$. A restriction 310 is used to adjust the level of pressure as indicated by the pressure gauge 312. Ions focused by an ion funnel 314 and through a skimmer 316 are introduced into the channel 318 of a segmented DMS 320 accommodated in a second vacuum chamber 322 maintained at pressure $P_2$ by a vacuum pump 324. Pressure is monitored by a pressure gauge 326 and pressure levels can be adjusted by adjusting restriction 310. Ions transported successfully through the DMS pass through an aperture 328 and enter a consecutive vacuum compartment 330 housing an octapole device 332 for collisionally cooling ions. Pressure is maintained by a turbo-molecular pump 334 and levels are monitored by a gauge 336. Ions are then passed onto the mass analyzer region 338. When it is desired to transmit ions without filtering using the DMS, the asymmetric waveform may be removed and instead applied is a radially confining RE voltage, to simply transmit a wide range of m/z and independent of their mobility.

Figure 11:
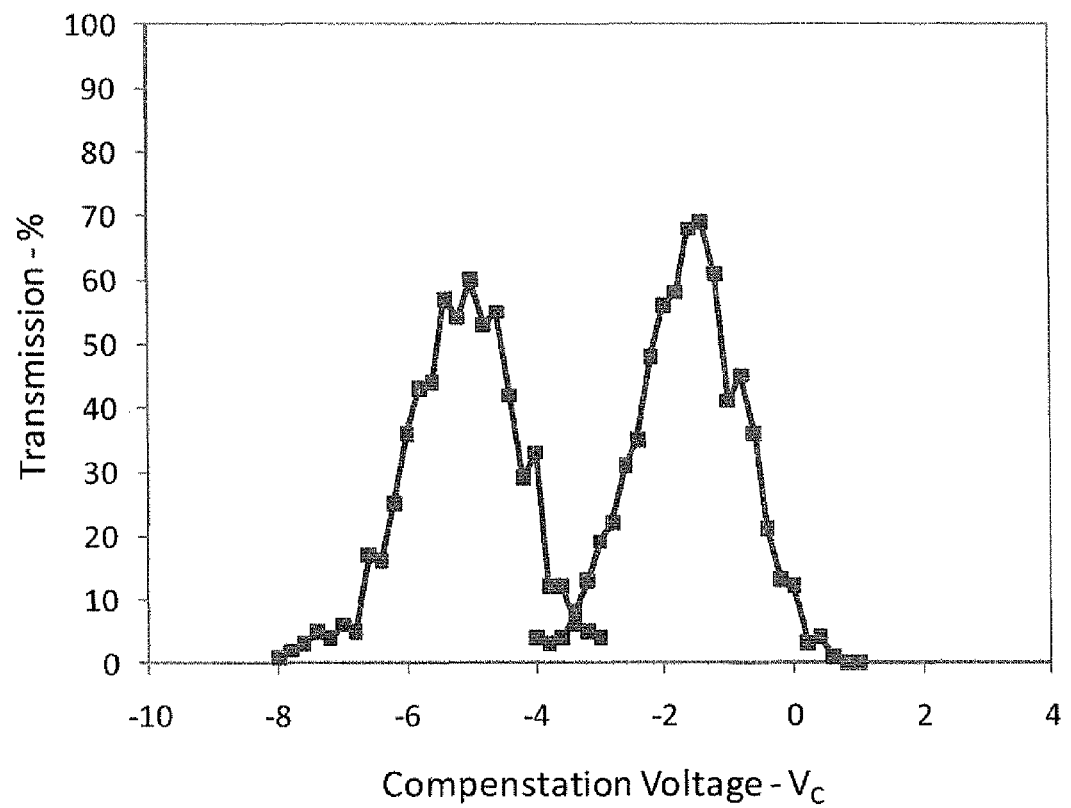
FIG. 11 is a DMS spectrum obtained with a dodecapole DMS geometry of FIGS. 2 and 3, with 5 mm diameter, at 30 Torr.

With reference to FIG. 11, ion simulations according to differential mobility showing separation of ions were conducted for the dodecapole geometry. Throughout these simulations the axial gas flow through the device was set to 100 $ms^{-1}$ and the ion residence time was approximately 0.7 ms. The dipole field was applied along the X axis and the pressure was set at 30 Torr. The voltage was applied to attain an E/N value of ~250 Td. FIG. 11 shows an example of separation of two model ions, $C_3H_7^+$ and $C_3H_5^+$, in the device, the plot being generated by applying the asymmetric waveform to generate the alternating dipole at a frequency of 1 MHz and scanning the compensation voltage. Baseline separation is obtained and ions are ~2V wide at full-width half maximum. Transmission is approximately 65%.

The effect of superimposing a quadrupole field on the transmission and resolution is discussed below, with reference to FIGS. 12 and 13.

FIG. 12a shows voltage ratios used to generate a standard dipole field, which can be applied as RF and/or DC compensating field for the case of the dodecapole geometry.

Within the analytical space, this field corresponds to a dipole field that is generated in the planar DMS where in use ions oscillate along the X direction.

FIG. 12b shows the voltage ratios used to generate a quadrupole field in the analytical space of the DMS. Such a field may be superimposed onto the said dipole field already described by adjusting the amplitude of the waveforms applied to each electrode accordingly.

By combining, that is superimposing, the fields shown in FIGS. 12a and 12b the transmission of ions improves, as the confining quadrupole field confines those ions which are selected according to their differential mobilities by dipole asymmetric RF and DC compensating dipole fields.

Radial focusing is achieved only by applying an additional DC quadrupole field in addition to the RF quadrupole field and carefully adjusting the relative amplitudes. The amplitude of the RF and DC quadrupole fields is considerably lower compared to the magnitude of the dipole. It should noted that the negative high voltage is along X direction, and the positive high voltage pulse of the rectangular waveform is applied along the Y direction.

Efficient focusing can be demonstrated by simulation and the results are shown in FIGS. 13a and 13b. In attaining the DMS spectrum of FIG. 13a the following voltages were applied: RF dipole $V_H$=600, $V_L$=−257.14, and for the RF quadrupole $V_H$=40, $V_L$=−17.14, for the DC quadrupole $V_Q$=5. These conditions provide high transmission over a wide range of compensating voltages, however, resolution is reduced.

By reducing the strength of the quadrupole field to: RF quadrupole $V_H$=20, $V_L$=−8.57 and DC quadrupole $V_Q$=3, resolution is maintained while transmission has been improved by ~20% compared to that of a pure dipole field, as shown in FIG. 13b.

Thus, the superposition of a quadrupole field can enhance the transmission without degradation of resolving power, or alternatively, the strength of the quadrupole field may be increased to enhance transmission further and to controllable reduce the resolution. This latter facility is useful when the DMS is operated as a noise reduction device.

Further simulations have been performed to investigate the effect of operating pressures and waveform frequencies on transmission and resolution of the DMS.

Low Pressure

Simulations at 0.01 mbar and a multipole geometry with inscribed radius of 2.5 mm indicate that the number of collisions during one waveform period is insufficient and diffusion is pronounced. Transmission of ions through the DMS channel is practically zero. Increasing the pressure by one order of magnitude, that is 0.1 mbar, has a significant impact on the performance of the DMS. Simulations results using the two model ions discussed above indicate that transmission is ~5%, sufficient for demonstrating ion separation in the DMS. Pressures above 0.1 mbar appear mostly appropriate for reducing diffusion and enhancing transmission. Also, it must be noted that diffusional effects can only be counterbalanced using higher-order fields at pressures above 0.1 mbar.

Low Frequency

Further simulation analysis of the DMS operation at a pressure of 10 mbar indicates that for the case of the two model ions examined above, reducing frequency from 1 MHz to 10 KHz has a significant impact on ion transmission. The amplitude of ion oscillation can be wide compared to the dimensions of the device (e.g. as high as 2 mm) and ion losses on the DMS electrodes become severe, simulation shows transmission <1%. The amplitude of ion oscillation must be maintained small compared to the dimensions of the analytical space. For example, the amplitude of ion oscillation at 1 MHz for both model ions examined above is ~0.5 mm, that is, one order of magnitude smaller than the 5 mm analytical space used in the calculations.

High Frequency

The useful operating area of the DMS in terms of frequency is limited by the transit times of the ions, as described above. Further simulation studies demonstrate that despite enhancing transmission to >80%, ion separation becomes poor, such that there is no observed separation of the $C_3H_7^+$ and $C_3H_5^+$ ions when operating at 25 MHz.

The invention claimed is:

1. An ion analysis apparatus comprising:
an ionization source for generating ions from a sample; and
an ion detector;
wherein in use ions travel along an ion optical axis from the ionization source to the ion detector, the apparatus further comprising:
a vacuum enclosure including
a first vacuum region containing differential ion mobility means; and
a second vacuum region containing a mass analyzer;
pumping means configured to provide a pressure in the second vacuum region that is lower than the pressure in the first vacuum region;

an ion inlet connecting the ionization source to the first vacuum region, wherein the first vacuum region is located before the second vacuum region on the ion optical axis such that in use ions generated from the sample undergo differential ion mobility analysis before mass analysis;

and wherein in use the first vacuum region including the differential ion mobility means is at a pressure in the range 2 kPa to 40 kPa and the differential ion mobility means is driven by an asymmetric waveform having a frequency in the range 20 kHz to 25 MHz;

and wherein an apparatus includes gas flow means for establishing a flow of gas into the first vacuum region so as to provide a gas medium for the differential ion mobility means.

2. An ion analysis apparatus according to claim 1, wherein the frequency is in the range 1.5 MHz to 5 MHz.

3. An ion analysis apparatus according to claim 1, wherein the analytical gap, d, of the differential ion mobility means is in the range 1 mm to 15 mm.

4. An ion analysis apparatus according to claim 1, wherein the gas provided by the gas flow means is different from the gas in the ionization source.

5. An ion analysis apparatus according to claim 1, wherein the asymmetric waveform applied to the differential ion mobility means is provided by a digital waveform generator.

6. An ion analysis apparatus according to claim 1, wherein the apparatus includes a waveform generator configured to apply the asymmetric waveform to at least one electrode of the differential ion mobility means; and waveform switching means to switch between a first waveform and a second waveform.

7. An ion analysis apparatus according to claim 6, wherein the waveform is switchable between a first waveform that has a duty cycle of 50% and a second waveform that has a duty cycle that is not 50%.

8. An ion analysis apparatus according to claim 6, wherein the waveform is switchable between an ion transmission mode and an ion separation mode.

9. An ion analysis apparatus according to claim 6, wherein the apparatus is configured to change the duty cycle of the waveform in the range 0.05 to 0.5.

10. An ion analysis apparatus according to claim 1, wherein the apparatus includes ion transport electric field means which in use provide an electric field that urges the ions through the differential ion mobility means.

11. An ion analysis apparatus according to claim 1, wherein the second vacuum region includes a collisional cooling cell located before the mass analyzer.

12. An ion analysis apparatus according to claim 1, wherein the apparatus includes, in the first vacuum region, gas flow modifying means associated with the ion inlet, which gas flow modifying means is configured to provide in use a substantially laminar gas flow to the differential ion mobility means.

13. An ion analysis apparatus according to claim 1, wherein the differential ion mobility means comprises an electrode arrangement selected from:
(a) two planar parallel electrodes;
(b) two concentric cylindrical electrodes; and
(c) a multipole wherein a plurality of elongate electrodes are arranged circumferentially around a common axis, with the longitudinal axes of the electrodes being parallel.

14. An ion analysis apparatus according to claim 13, wherein the differential ion mobility means comprises a multipole and wherein the apparatus includes a waveform generator configured to provide (i) a dipole field and (ii) a higher order field within the multipole.

15. An ion analysis apparatus according to claim 1, wherein in use the pressure in the second vacuum region is less than $10^{-4}$ kPa.

16. An ion analysis apparatus according to claim 1, wherein the mass analyzer is selected from a quadrupole filter, time of flight analyzer (TOF), linear RF ion trap and electrostatic ion trap.

17. A method of analyzing ions, which method comprises the steps of:
(a) generating ions from a sample in an ionization source;
(b) delivering the ions through an ion inlet into a first vacuum region of a vacuum enclosure;
(c) in the first vacuum region, prior to mass analysis of the ions, conducting differential ion mobility analysis of the ions;
(d) after differential ion mobility analysis, delivering the ions to a second vacuum region of the vacuum enclosure; and
(e) in the second vacuum region conducting mass analysis of the ions;

and wherein in use the first vacuum region including the differential ion mobility means is at a pressure in the range 2 kPa to 40 kPa and the differential ion mobility means is driven by an asymmetric waveform having a frequency in the range 20 kHz to 25 MHz;

and wherein the method includes establishing a flow of gas into the first vacuum region so as to provide a gas medium for the said differential ion mobility analysis.

18. An ion analysis apparatus comprising:
an ionization source for generating ions from a sample; and
an ion detector;
wherein in use ions travel along an ion optical axis from the ionization source to the ion detector, the apparatus further comprising:
a vacuum enclosure including
a first vacuum region containing differential ion mobility means; and
a second vacuum region containing a mass analyzer;
pumping means configured to provide a pressure in the second vacuum region that is lower than the pressure in the first vacuum region;
an ion inlet connecting the ionization source to the first vacuum region,
the first vacuum region being located before the second vacuum region on the ion optical axis such that in use ions generated from the sample undergo differential ion mobility analysis before mass analysis,
wherein the differential ion mobility means comprises a multipole wherein a plurality of elongate electrodes are arranged circumferentially around a common axis, with the longitudinal axes of the electrodes being parallel,
and wherein the apparatus includes a waveform generator configured to provide (i) a dipole field and (ii) a higher order field within the multipole.

19. A method of analyzing ions, which method comprises the steps of:
(a) generating ions from a sample in an ionization source;
(b) delivering the ions through an ion inlet into a first vacuum region of a vacuum enclosure;
(c) in the first vacuum region, prior to mass analysis of the ions, conducting differential ion mobility analysis of the ions;
(d) after differential ion mobility analysis, delivering the ions to a second vacuum enclosure; and (e) in the second vacuum region conducting mass analysis of the ions;
wherein step (c) includes conducting differential ion mobility analysis with a multipole comprising a plurality of elongate electrodes arranged circumferentially around a common axis, with the longitudinal axes of the electrodes being parallel,
and wherein step (c) includes applying (i) a dipole field and (ii) a higher order field within the multipole.

* * * * *